United States Patent [19]
Castro et al.

[11] Patent Number: 6,004,326
[45] Date of Patent: Dec. 21, 1999

[54] METHOD AND INSTRUMENTATION FOR IMPLANT INSERTION

[75] Inventors: Salvatore Castro, Seymour, Conn.; Christine M. Tompkins, Washington, D.C.

[73] Assignee: United States Surgical, Norwalk, Conn.

[21] Appl. No.: 08/926,806

[22] Filed: Sep. 10, 1997

[51] Int. Cl.$^6$ .................................................. A61B 17/00
[52] U.S. Cl. ........................................................ 606/99
[58] Field of Search ............................ 606/99, 61–80, 606/86–88, 96–98, 104; 128/898; 604/158, 164, 167, 256, 264; 623/17

[56] References Cited

U.S. PATENT DOCUMENTS

| | | |
|---|---|---|
| D. 374,283 | 10/1996 | Michelson . |
| D. 397,436 | 8/1998 | Michelson . |
| 3,486,505 | 12/1969 | Morrison . |
| 3,848,601 | 11/1974 | Ma et al. . |
| 3,867,932 | 2/1975 | Huene . |
| 3,916,907 | 11/1975 | Peterson . |
| 4,059,115 | 11/1977 | Junashev et al. . |
| 4,328,593 | 5/1982 | Sutter et al. . |
| 4,501,269 | 2/1985 | Bagby . |
| 4,545,374 | 10/1985 | Jacobson . |
| 4,573,448 | 3/1986 | Kambin . |
| 4,677,972 | 7/1987 | Tornier . |
| 4,743,256 | 5/1988 | Brantigan . |
| 4,834,757 | 5/1989 | Brantigan . |
| 4,877,020 | 10/1989 | Vich . |
| 4,878,915 | 11/1989 | Brantigan . |
| 4,936,851 | 6/1990 | Fox et al. . |
| 4,961,740 | 10/1990 | Ray et al. . |
| 4,978,350 | 12/1990 | Wagenknecht . |
| 5,015,247 | 5/1991 | Michelson . |
| 5,015,255 | 5/1991 | Kuslich . |
| 5,026,373 | 6/1991 | Ray et al. . |
| 5,055,104 | 10/1991 | Ray . |
| 5,062,845 | 11/1991 | Kuslich et al. . |
| 5,195,541 | 3/1993 | Obenchain . |
| 5,263,953 | 11/1993 | Bagby . |
| 5,313,962 | 5/1994 | Obenchain . |
| 5,352,231 | 10/1994 | Brumfield et al. . |
| 5,354,302 | 10/1994 | Ko . |
| 5,357,983 | 10/1994 | Mathews . |
| 5,358,511 | 10/1994 | Gatturna et al. . |

(List continued on next page.)

FOREIGN PATENT DOCUMENTS

WO 9627345  12/1996  WIPO .

OTHER PUBLICATIONS

Posterior Lumbar Interbody Fusion Made Simple, Neurological Surgery Associates of Cincinnati, Inc.
Scientix Brochure, Cage CH, "Lumbar Spacing Cages".
Intervertebral Body Fusion By the Use of Posterior Bone Dowel, Benjamin R. Wilterberger, M.D., pp. 69–79.
A Technique of Posterior Cervical Fusion for Instability of the Cervical Spine, Davey et al. (1984).
Surgical Dynamics Brochure, Ray Ti for Interbody Fusion, Investigational Device, (1994).
Stryker Implants Brochure, Ogival Interbdoy Cage, Surgical Technique.
Unilateral Posterior Lumbar Interbody Fusion; Simplified Duel Technique, Blume (1984).
Sofamor Danek™ The Spine Specialist$^{SM}$, "Laparoscopic Bone Dowel Surgical Technique", 1995.

*Primary Examiner*—Michael Buiz
*Assistant Examiner*—Vikki Trinh

[57] ABSTRACT

A laparoscopic surgical retractor for use during a laparoscopic spinal procedure, includes an elongated sleeve member having proximal and distal end portions and defining a longitudinal opening therethrough and a valve assembly mounted to the proximal end portion of the elongated sleeve member for sealing a surgical instrument introduced within the longitudinal opening of the sleeve member. The distal end portion is configured for insertion at least partially into an intervertebral space between adjacent opposed vertebrae to distract the adjacent vertebrae. A method for inserting a fusion implant with the use of the retractor is also disclosed.

22 Claims, 19 Drawing Sheets

U.S. PATENT DOCUMENTS

| | | |
|---|---|---|
| 5,395,317 | 3/1995 | Kambin . |
| 5,400,805 | 3/1995 | Warren . |
| 5,423,825 | 6/1995 | Levine . |
| 5,431,658 | 7/1995 | Moskovich . |
| 5,439,464 | 8/1995 | Shapiro . |
| 5,454,811 | 10/1995 | Huebner . |
| 5,458,638 | 10/1995 | Kuslich et al. . |
| 5,470,334 | 11/1995 | Ross et al. . |
| 5,480,403 | 1/1996 | Lee . |
| 5,484,437 | 1/1996 | Michelson . |
| 5,489,307 | 2/1996 | Kuslich et al. . |
| 5,489,308 | 2/1996 | Kuslich et al. . |
| 5,505,732 | 4/1996 | Michelson . |
| 5,522,899 | 6/1996 | Michelson . |
| 5,534,031 | 7/1996 | Matsuzaki et al. . |
| 5,549,679 | 8/1996 | Kuslich . |
| 5,554,191 | 9/1996 | Lahille et al. . |
| 5,562,736 | 10/1996 | Ray et al. . |
| 5,571,109 | 11/1996 | Bertagnoli . |
| 5,571,189 | 11/1996 | Kuslich . |
| 5,571,192 | 11/1996 | Schönhöffer . |
| 5,591,207 | 1/1997 | Coleman . |
| 5,591,235 | 1/1997 | Kuslich . |
| 5,593,409 | 1/1997 | Michelson . |
| 5,609,635 | 3/1997 | Michelson . |
| 5,609,636 | 3/1997 | Kohrs et al. . |
| 5,645,549 | 7/1997 | Boyd et al. . |
| 5,653,761 | 8/1997 | Pisharodi . |
| 5,741,253 | 4/1998 | Michaelson . |

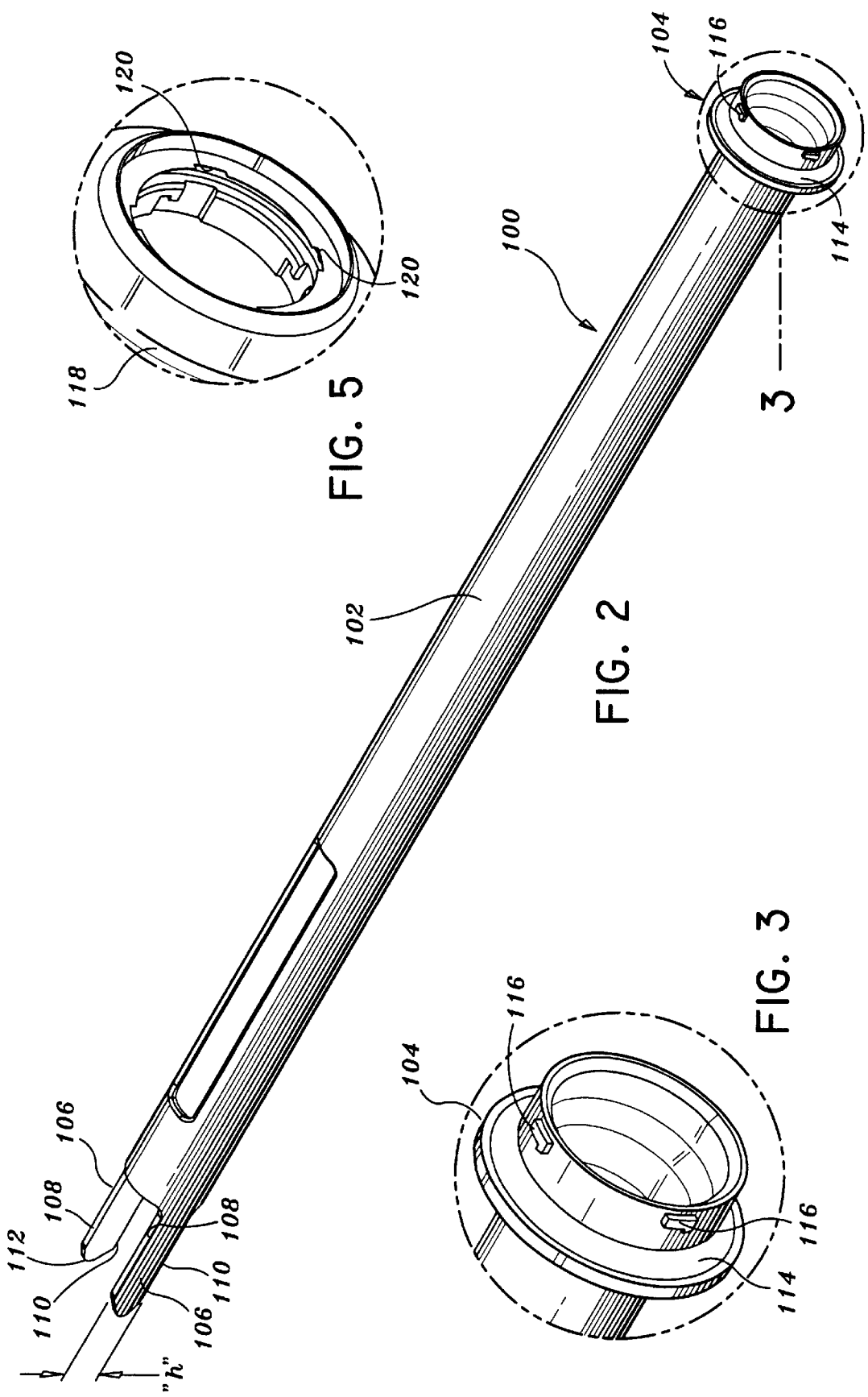

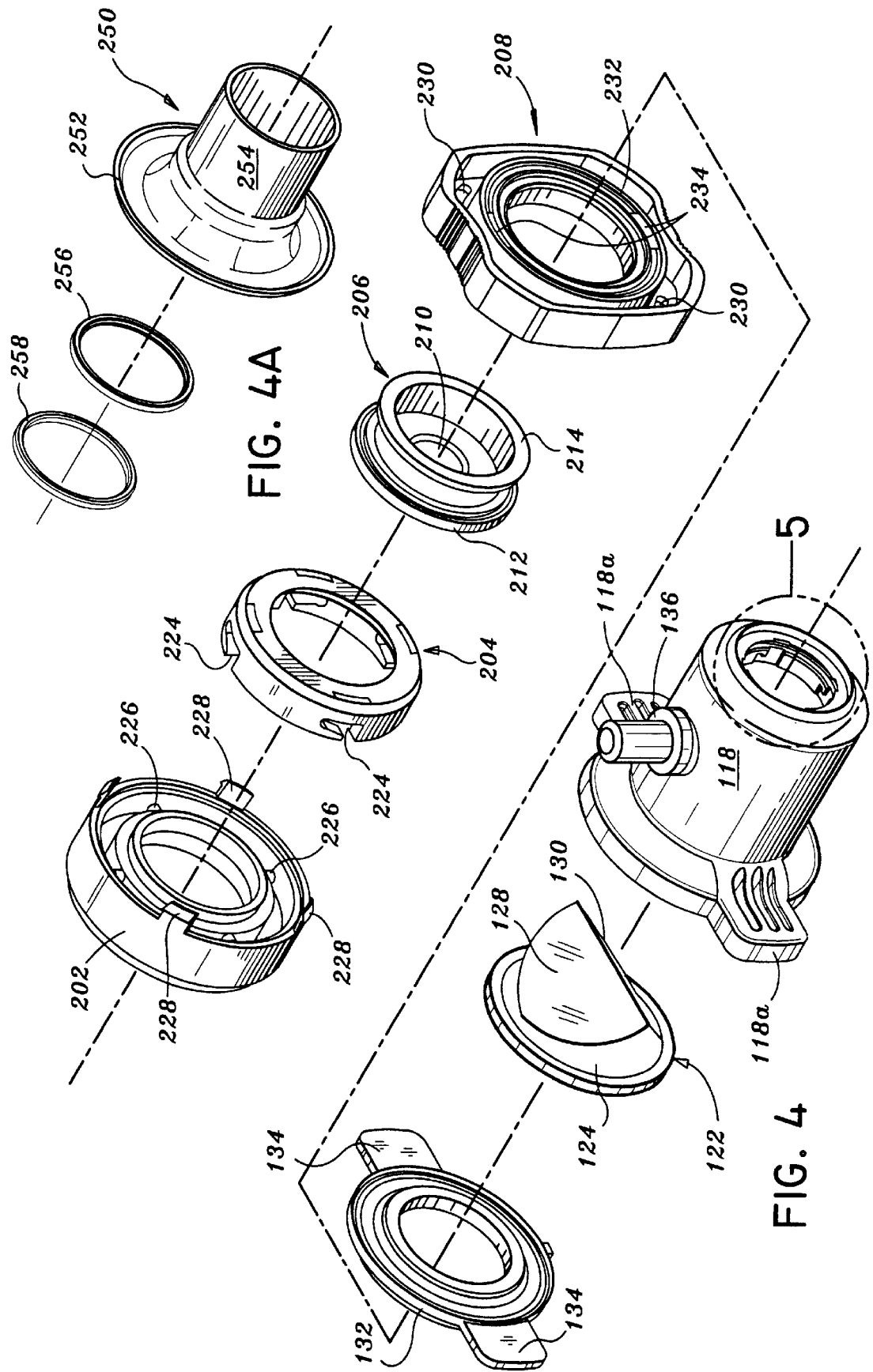

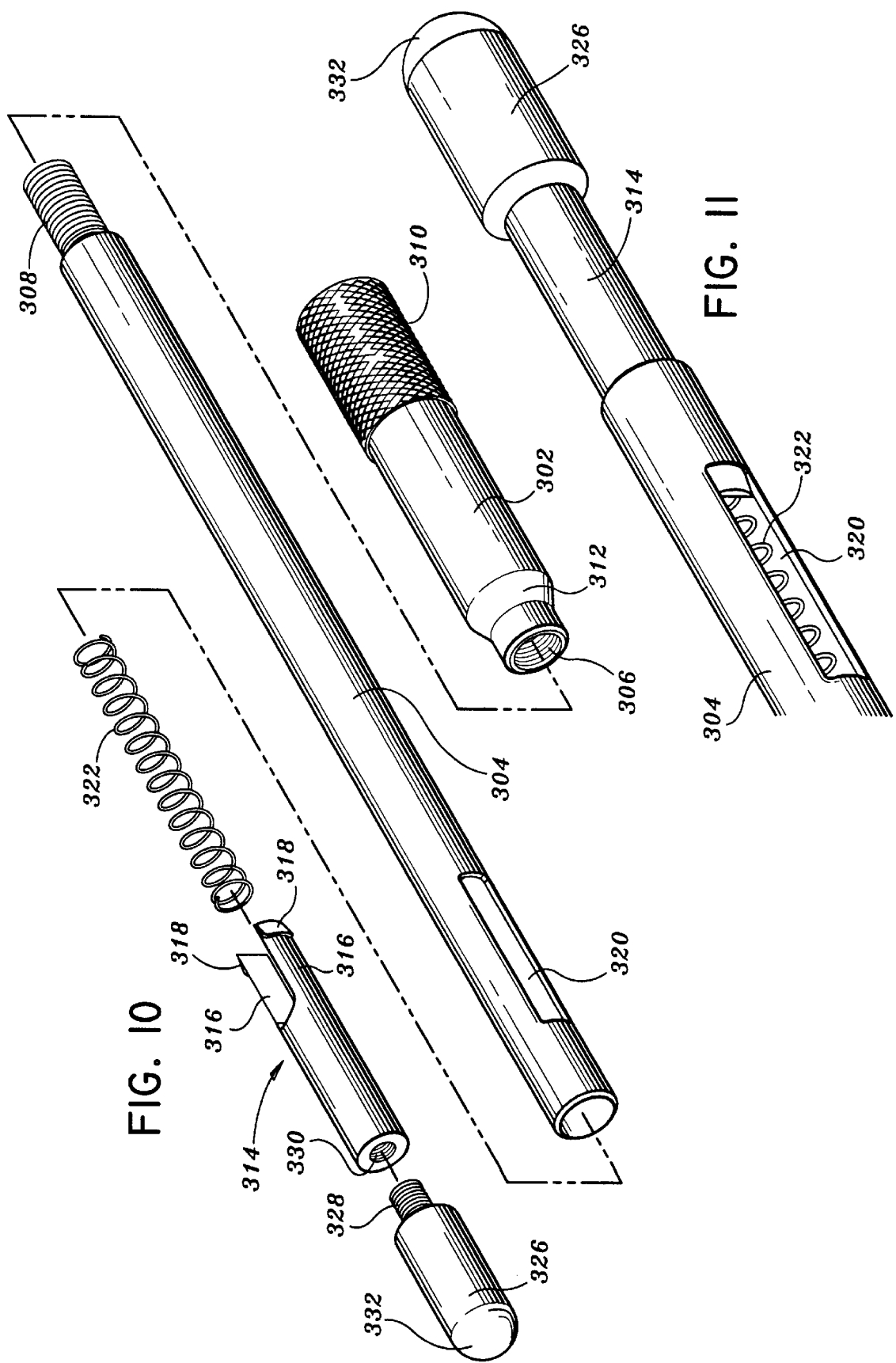

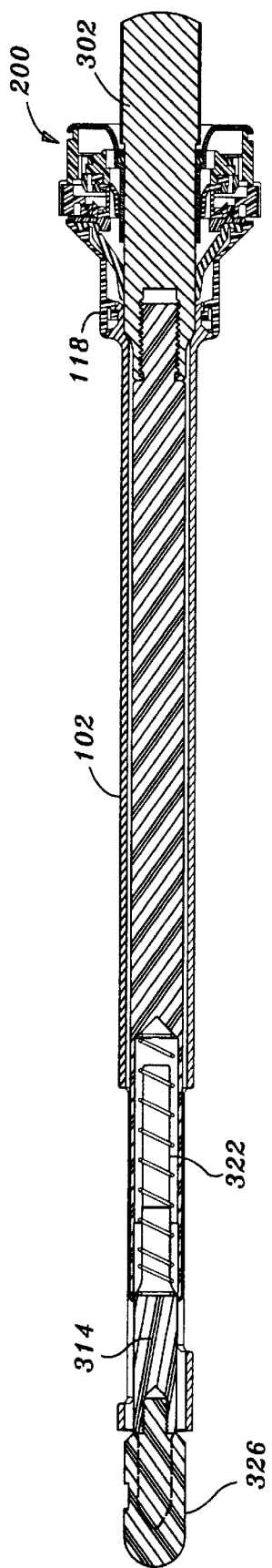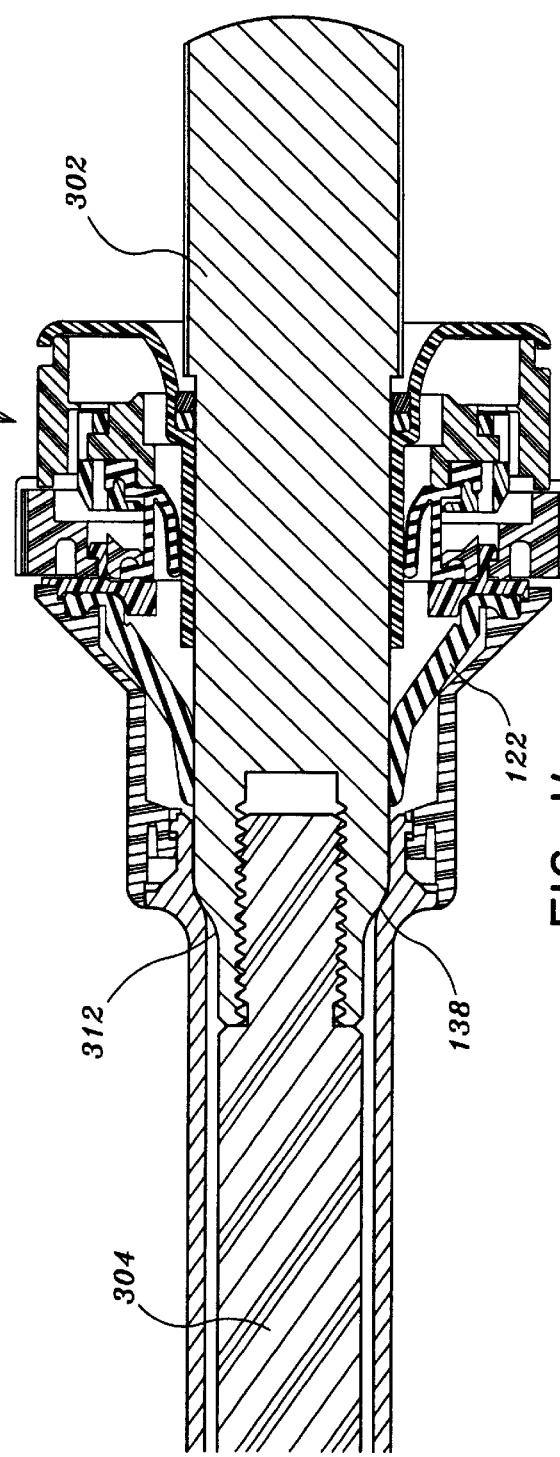
FIG. 13
FIG. 14

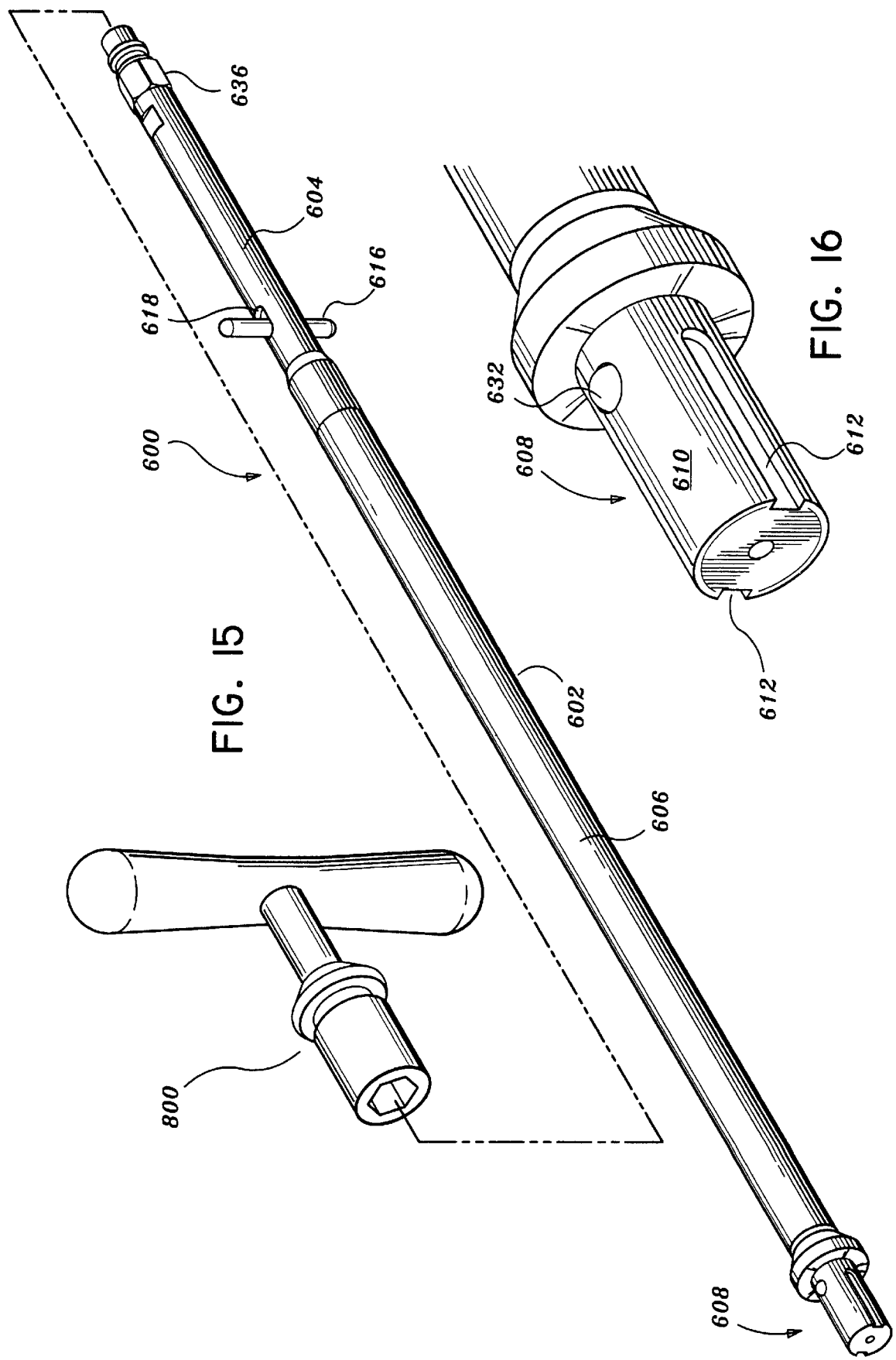

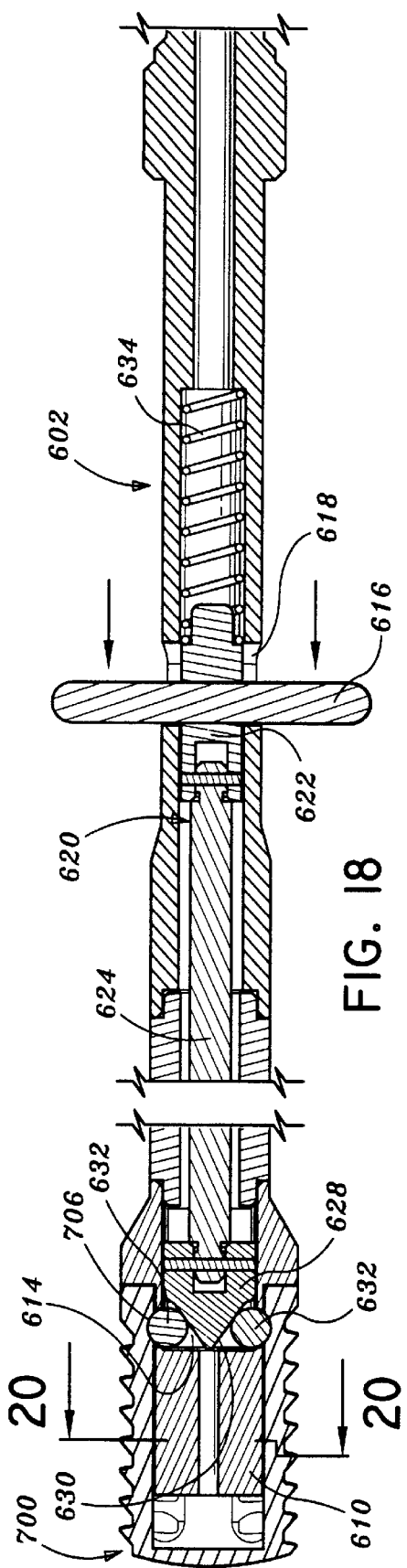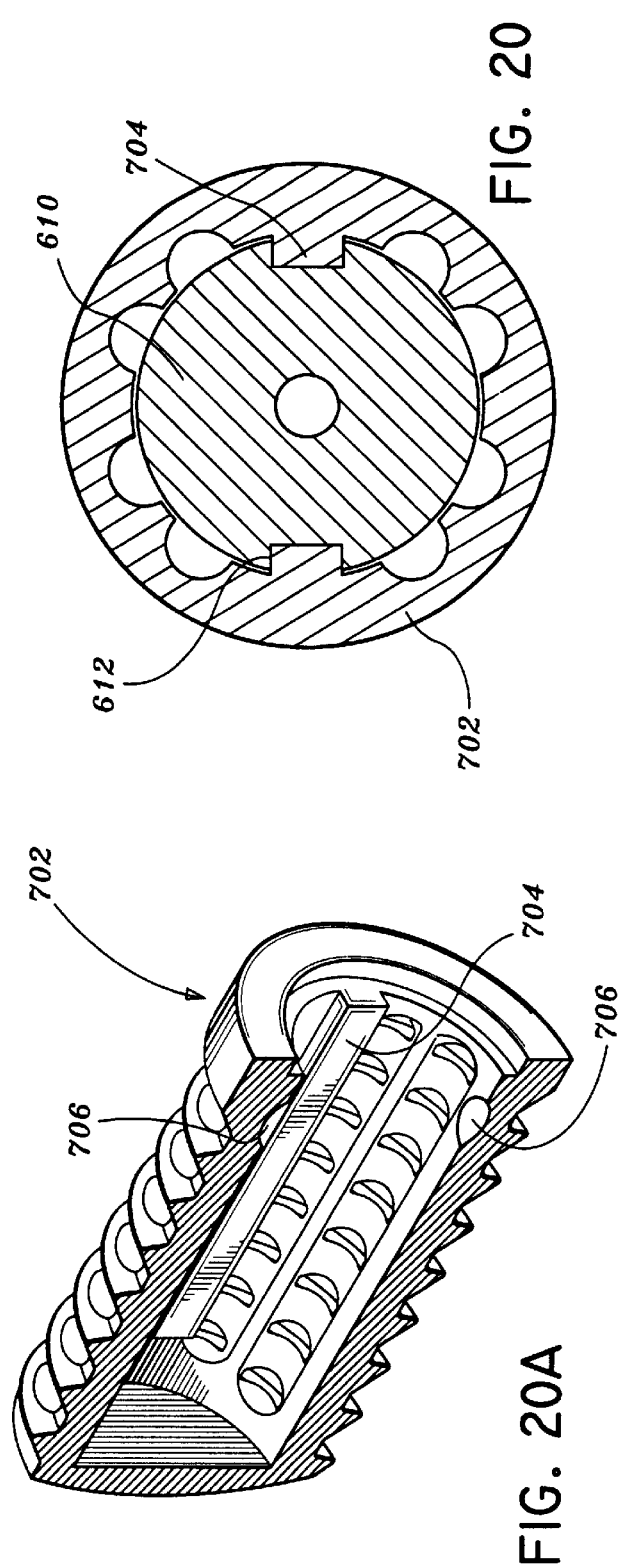
FIG. 18
FIG. 20
FIG. 20A

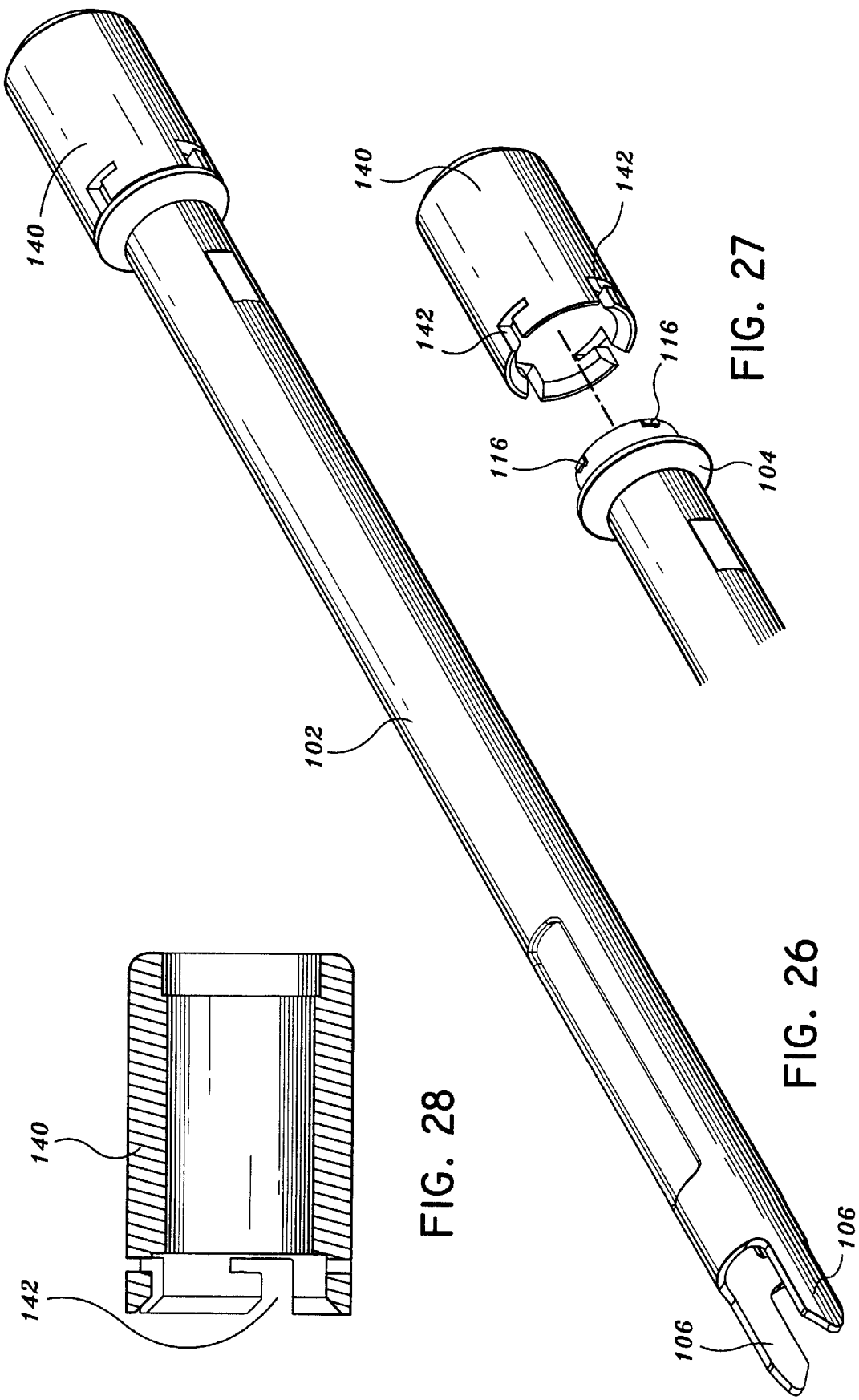

METHOD AND INSTRUMENTATION FOR IMPLANT INSERTION

BACKGROUND

1. Technical Field

The present disclosure generally relates to a method and associated instrumentation for implant insertion and, in particular, to a method and instrumentation for insertion of spinal implants to facilitate fusion of adjacent vertebral bodies.

2. Background of the Related Art

A large number of orthopedic procedures involve the insertion of either natural or prosthetic implants into bone or associated tissues. These procedures include, for example, ligament repair, joint repair or replacement, non-union fractures, facial reconstruction, spinal stabilization and spinal fusion. In a typical procedure, an insert, dowel or screw is inserted into a prepared bore formed in the bone or tissues to facilitate repair and healing. See, for example, U.S. Pat. No. 5,470,334 to Ross et al.; U.S. Pat. No. 5,454,811 to Huebner; U.S. Pat. No. 5,480,403 to Lee et al.; U.S. Pat. No. 5,358,511 to Gatturna et al.; and U.S. Pat. No. 4,877,020 to Vich.

Some implants are particularly configured with cavities and bores to facilitate bony ingrowth and enhance anchoring of the implant at the insertion site. See, for example, U.S. Pat. No. 4,328,593 to Sutter et al.; U.S. Pat. No. 4,936,851 to Fox et al.; and U.S. Pat. No. 4,878,915 to Brantigan. Other specialized implants include fusion cages having internal cavities to receive bone growth stimulation materials such as bone chips and fragments. See, for example, U.S. Pat. No. 4,501,269 to Bagby; U.S. Pat. No. 4,961,740 to Ray et al.; U.S. Pat. No. 5,015,247 to Michaelson; and U.S. Pat. No. 5,489,307 to Kuslich et al. These types of implants are particularly well suited for intervertebral spinal fusion procedures necessitated by injury, disease or some degenerative disorder of the spinal disc. Subsequently, there may be progressive degeneration leading to mechanical instability between adjacent vertebrae necessitating, direct fusion of the vertebrae while maintaining a pre-defined intervertebral space. This fusion may be accomplished by the insertion of one or more of the specialized implants as discussed above and also discussed in U.S. Pat. No. 5,026,373, the contents of which are incorporated herein by reference.

Both anterior (transabdominal) and posterior surgical approaches are used for interbody fusions of the lumbar spine. Fusions in the cervical area of the spine are performed using an anterior or posterior approach as well. Typically, an implant such as a plug, dowel, prosthesis or cage is inserted into a preformed cavity inside the interbody, interdiscal space. Since it is desirable in these procedures to promote a "bone to bone" bridge, connective tissue and at least a portion of the distal tissue is removed. Preferably, relatively deep cuts are made in the adjacent bones in order to penetrate into the softer, more vascularized cancerous region to facilitate bone growth across the implant.

One of the more critical tasks performed in the insertion of a surgical fusion implant, particularly, in intervertebral spinal fusion, is the formation of the implant receiving cavity or bore within the adjacent vertebrae. More particularly, the drilled bore must be equally centered within the intervertebral space and preferably parallel to the vertebral end plates to ensure removal of equal portions of bone from the adjacent vertebrae throughout the length of the cut and subsequent appropriate seating of the implant relative to the vertebral bodies.

Surgical instruments for facilitating spinal fusion implant insertion are known. For example, U.S. Pat. No. 5,484,437 to Michelson discloses a method and apparatus incorporating an outer and an inner sleeve arrangement. The outer sleeve has teeth at one end which are driven directly into the posterior surface of the adjacent vertebrae. The inner sleeve is positioned within the outer sleeve and serves to guide instruments such as a drill used to form the implant receiving bore. U.S. Pat. No. 5,487,307 to Kuslich et al.; U.S. Pat. No. 5,015,247 to Michelson; and U.S. Pat. No. 4,878,915 to Brantigan disclose similar arrangements. Other arrangements include the use of guide rods which are placed in pilot holes formed in the vertebral bodies. The guide rods guide a bore forming hollow drill into the intervertebral space.

Although current instrumentation and methods associated therewith for enhancing the placement of spinal fusion implants have been generally effective for their intended purposes, there exists certain limitations with the design of this instrumentation which detract from their usefulness. For example, the arrangement disclosed in the Michelson '437 patent and similar arrangements do not provide for automatic alignment of the outer sleeve to ensure that the bore formed by a drill introduced into the outer sleeve is in optimal alignment for a tapping procedure (if required) and reception of the spinal implant. Rather, such orientation is dependent directly upon the skill of the surgeon. Moreover, the outer sleeve, which is mounted only at its extreme distal end to the posterior surface of the adjacent vertebrae, is subject to disorientation or dislodgment during insertion and/or removal of the drill and/or tapping instrument. Similarly, the use of guide rods increases the number of steps required to implant the fusion cage and is also subject to possible misalignment.

U.S. patent application Ser. No. 08/615,379, filed Mar. 14, 1996 discloses a novel method and associated instrumentation to facilitate the introduction of a fusion implant. The instrumentation disclosed in the '379 application ensures optimal alignment of the drilled bore for reception of the fusion implant and, if appropriate, for bore tapping procedures. The instrumentation includes a surgical retractor and a drill. The retractor is configured for distracting adjacent vertebral bodies to facilitate the insertion and application of an implant, for providing a cannula for insertion of auxiliary instruments, e.g., the drill, and for ensuring proper alignment of the instrumentation and accurate insertion of the implant. The instrumentation and method disclosed in the '379 application is well suited for implanting an implant such as the aforedescribed Ray '373 fusion cage.

Over the last few years, the number of laparoscopic/endoscopic procedures has increased. In such procedures, instead of creating a large incision in the patient as in conventional approaches, surgery is performed through small incisions in the patient with trocar cannulas providing access ports for the surgical instrumentation. This minimally invasive approach to surgery results in less trauma to the patient and a quicker recovery time.

Thus, it would be advantageous to provide surgical instrumentation to facilitate minimally invasive spinal fusion procedures and particularly to facilitate minimally invasive placement of spinal fusion implants.

SUMMARY

Accordingly, the present disclosure is directed to further improvements and adaptations to the instrumentation and method disclosed in the '379 application to facilitate a laparoscopic approach to spinal fusion. Generally, the present disclosure is directed to a laparoscopic surgical retractor for use during a laparoscopic spinal procedure, including an elongated sleeve member having proximal and distal end portions and defining a longitudinal opening therethrough, and a valve assembly mounted to the proximal end portion of the elongated sleeve member for sealing a surgical instrument introduced within the longitudinal opening of the sleeve member. The distal end portion is configured for insertion at least partially into an intervertebral space between adjacent opposed vertebrae to distract the adjacent vertebrae. In one embodiment, the distal end portion of the sleeve member includes two spaced apart retractor arms having first and second supporting surfaces. Each retractor arm defines a dimension between the first and second supporting surfaces sufficient to distract the opposed tissue portions upon insertion thereof. The first and second supporting surfaces of each retractor arm are preferably substantially planar.

The valve assembly may be releasably mounted to the retractor. Preferably, the valve assembly includes a valve body defining at least one opening configured and dimensioned to permit entry of the instrument and a valve member formed of a resilient material and defining an aperture in general alignment with the opening of the valve body. The aperture is configured and dimensioned such that upon insertion of the elongated object into the aperture the resilient material resiliently engages the outer surface of the object in a substantially fluid-tight manner.

A converter may be provided with the valve assembly. The converter is insertable within the aperture of the valve member to protect the integrity of the valve body of the valve assembly. The converter includes a seal member defining a seal aperture adapted to form a seal about the outer surface of an object (e.g., a surgical instrument) inserted therethrough. Various-sized converters are contemplated to be used with different-sized instruments.

An elongated impactor instrument may be provided to be positioned within the longitudinal opening of the sleeve member. The impactor instrument is utilized to facilitate mounting of the surgical retractor within the adjacent vertebrae. More particularly, the surgical retractor and the impactor instrument include corresponding engaging surfaces such that applying a distal force to the impactor causes the surgical retractor to be advanced distally within the adjacent vertebrae. The impactor instrument includes an elongated member and a distal impactor head configured to prevent entry of fluids within the surgical retractor when positioned within the longitudinal opening of the surgical retractor. The impactor head is also longitudinally movable relative to the elongated member so as to not enter the intervertebral space upon application of the distal force to the elongated member. The impactor head is spring biased distally.

In another embodiment, the laparoscopic surgical retractor for use during a laparoscopic procedure, includes an elongated sleeve member having proximal and distal end portions and defining a longitudinal opening therethrough. The distal end portion includes two spaced apart retractor arms having first and second supporting surfaces. Each retractor arm defines a dimension between the first and second supporting surfaces sufficient to distract the opposed tissue portions upon insertion thereof. A housing is mounted to the sleeve member and contains a seal member associated therewith. The seal member is adapted to prevent egress of insufflation gases in the absence of a surgical instrument. The housing may be releasably mounted to the sleeve member. The surgical retractor may further include a valve assembly releasably mounted to the housing. The valve assembly includes a valve housing and a valve member mounted to the valve housing and adapted to form a fluid-tight seal about an instrument inserted therethrough.

An apparatus for facilitating fusion of adjacent vertebrae is also provided. The apparatus comprises an insertion tool including an elongated member having a mounting portion disposed at the distal end thereof and a fusion implant releasably mounted to the mounting portion. The fusion implant includes a cage body defining a longitudinal bore and is positionable about the mounting portion of the insertion tool. At least one of the mounting portion of the insertion tool and the cage body of the fusion implant includes a rail extending in a longitudinal direction and wherein the other of the mounting portion and the cage body includes a groove extending in a longitudinal direction and being correspondingly dimensioned to receive the rail, to thereby prevent relative rotational movement of the insertion tool and the fusion implant.

The insertion tool includes a drive member extending within a bore of the elongated member and reciprocally longitudinally movable between first and second positions, and engaging structure disposed within the mounting portion. The engaging structure is movable between a disengaged position to disengage from the fusion implant corresponding to the first position of the drive member and an engaged position in engagement with the fusion implant corresponding to the second position of the drive member. The engaging structure includes an engaging ball at least partially disposed within a correspondingly dimensioned aperture of the mounting portion. The cage body preferably includes a recess defined in the interior surface thereof dimensioned to accommodate at least a portion of the engaging ball upon movement of the engaging ball to the engaged portion.

A method for performing a surgical spinal procedure is also disclosed. The method includes the steps of:

providing a laparoscopic surgical retractor including an elongated member having proximal and distal end portions and defining a longitudinal opening, the distal end portion including two spaced apart retractor arms having first and second supporting surfaces, the surgical retractor further including a valve assembly mounted to the proximal end portion of the elongated member and having a valve member associated therewith;

introducing a surgical instrument within the opening of the surgical retractor whereby the valve member of the valve assembly forms a fluid tight seal about an outer surface thereof; and performing the surgical procedure adjacent the distracted vertebrae with the surgical instrument.

BRIEF DESCRIPTION OF THE DRAWINGS

Preferred embodiments of the present disclosure are described hereinbelow with reference to the drawings wherein:

FIG. 2 is a perspective view of the surgical retractor,

FIG. 3 is an isolated perspective view of structure of the surgical retractor for mounting the retractor housing;

FIG. 4 is a perspective view with parts separated of the retractor housing and the valve assembly;

FIG. 4A is a perspective view with parts separated of the converter to be used with the valve assembly;

FIG. 5 is an isolated perspective view of the distal end of the retractor housing illustrating the structure for mounting the retractor housing to the retractor.

FIG. 10 is a perspective view with parts separated of the impactor instrument;

FIG. 11 is a perspective view of the distal end of the impactor instrument;

FIG. 13 is a cross-sectional view taken along the lines 13—13 of FIG. 12;

FIG. 14 is an enlarged cross-sectional view of the proximal end of the retractor housing, valve assembly and mounted surgical impactor;

FIG. 15 is an enlarged perspective view of the implant insertion instrument;

FIG. 16 is an enlarged perspective view of the distal end of the implant insertion instrument;

FIG. 18 is a side cross-sectional view of the implant insertion instrument with the fusion implant mounted thereto illustrating the engaged position of the insertion instrument;

FIG. 20 is a cross-sectional view taken along the lines 20—20 of FIG. 18 illustrating corresponding mounting structure of the insertion instrument and the fusion implant;

FIG. 20A is a perspective view with a portion cut-away of the fusion implant further illustrating the mounting rails extending within the internal cavity of the implant;

FIG. 26 is a perspective view of an alternative surgical retractor illustrating an adaptor mounted to the proximal end of the retractor;

FIG. 27 is a perspective view of the proximal end of the retractor of FIG. 26 illustrating the mounting arrangement between the adaptor and the retractor; and FIG. 28 is a side cross-sectional view of the adaptor of FIG. 27.

DETAILED DESCRIPTION OF THE PREFERRED EMBODIMENTS

The preferred embodiments of the method and instrumentation disclosed herein are discussed in terms of orthopedic spinal fusion procedures and instrumentation. It is also envisioned, however, that the disclosure is applicable to a wide variety of procedures including, but, not limited to ligament repair, joint repair or replacement, non-union fractures, facial reconstruction and spinal stabilization. The present method and instrumentation finds application in minimally invasive procedures including endoscopic and arthroscopic procedures wherein access to the surgical site is achieved through a cannula or small incision.

The following discussion will include a description of each instrument utilized in performing a spinal fusion method utilizing a laparoscopic anterior approach followed by a description of the preferred method for spinal fusion with the instrumentation in accordance with the present disclosure.

In the discussion which follows, the term "proximal", as is traditional, will refer to the portion of the structure which is closer to the operator, while the term "distal" will refer to the portion which is further from the operator.

Figure 1:
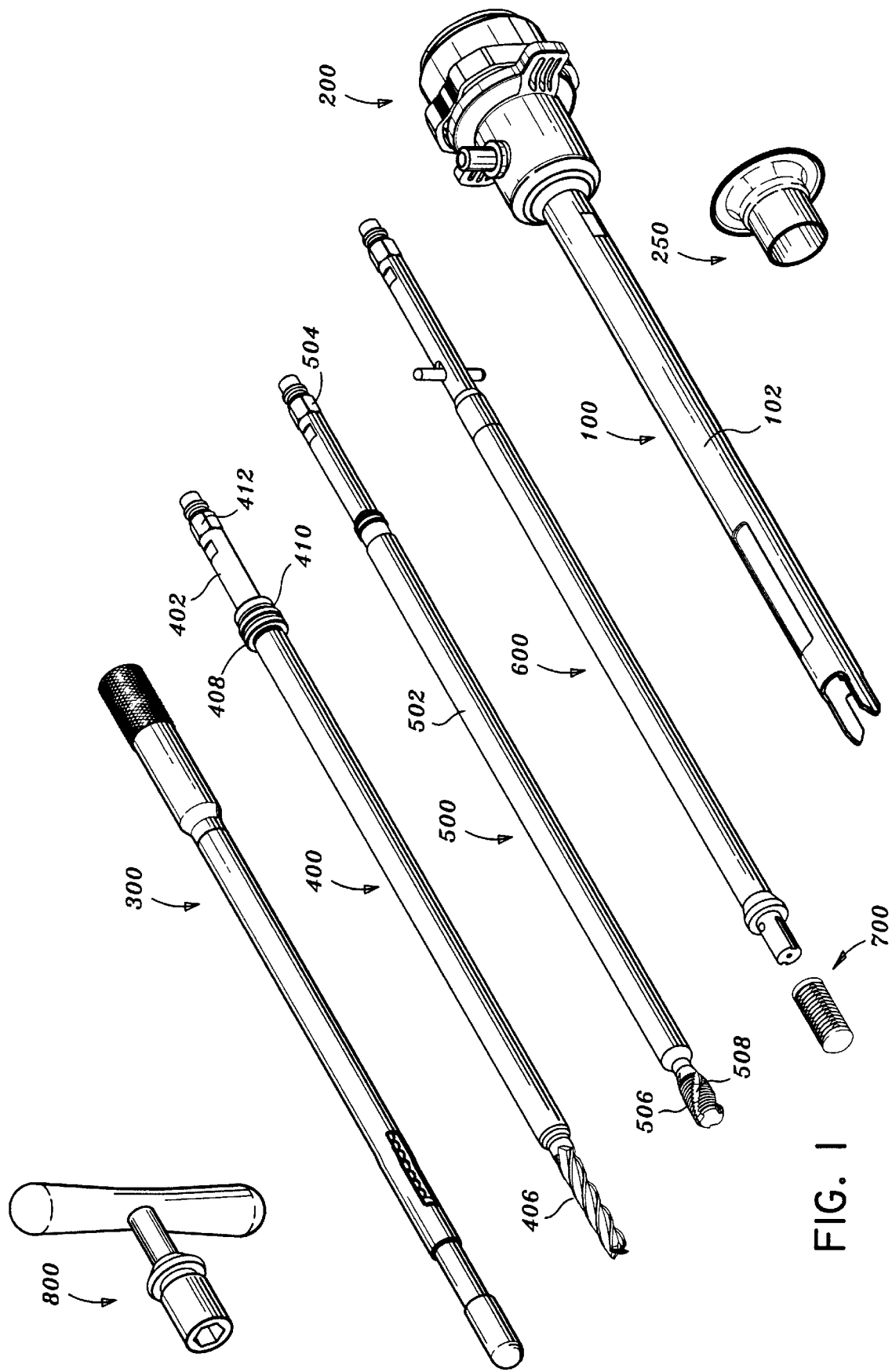
FIG. 1 is a perspective view of the surgical kit for performing a spinal fusion procedure through a laparoscopic approach illustrating, from bottom to top, a surgical retractor with mounted valve assembly and converter, an implant insertion apparatus, a surgical tapping instrument, a drilling instrument, an impactor instrument and a T-shaped handle.

Referring now to FIG. 1, there is illustrated in perspective view the surgical kit for performing a spinal fusion procedure through a laparoscopic approach in accordance with the principles of the present disclosure. The kit includes surgical retractor 100, valve assembly 200 detachably mountable to the surgical retractor, converter 250 to be used with the valve assembly 200, impactor instrument 300, drill instrument 400, tap instrument 500, implant insertion instrument 600, fusion implant 700 mountable to the insertion instrument 600 and T-shaped handle 800.

Surgical Retractor

With reference to FIGS. 2–4, in conjunction with FIG. 1, surgical retractor 100 will be discussed. Retractor 100 is similar to the surgical retractor disclosed in U.S. patent application Ser. No. 08/615,379, filed Mar. 14, 1996, the contents of which are incorporated herein by reference. Retractor 100 is configured for distracting adjacent vertebral bodies to facilitate the insertion and application of an implant, for providing a cannula for insertion of the instrument, and for ensuring proper alignment of the instrumentation and accurate insertion of the implant. Retractor 100 includes sleeve 102 with a mounting portion 104 disposed at the proximal end of the sleeve 102. Sleeve 102 includes at its distal end first and second diametrically opposed retractor arms 106 having first and second parallel vertebrae supporting surfaces 108, 110. The height "h" of each arm 106 (i.e., the distance between supporting surfaces 108, 110) corresponds to the height of the space between adjacent bony structures to be distracted. For example, in spinal implant application, the height "h" of each arm may range from about 0.28 inches to about 0.35 inches. Each arm 106 further includes tapered end portions 112 defining a general V-shaped configuration. End portions 112 facilitate insertion of retractor arms 106 within the surgical site, e.g., within the intervertebral space.

Mounting portion 104 of retractor 100 includes circumferential ledge 114 and a plurality (e.g., 4) of mounting ribs 116 radially arranged adjacent the circumferential ledge. A retractor housing 118 (FIG. 4) is releasably mounted to mounting portion 104. Retractor housing 118 defines a longitudinal opening for reception and passage of an elongated surgical instrument. The proximal end portion of retractor housing 118 defines a generally circular cross-section and possesses four equidistantly spaced mounting notches 120 (FIG. 5). Mounting notches 120 receive mounting ribs 116 of retractor sleeve 102 to releasably mount the retractor housing 118 to the sleeve 102. In an alternate embodiment, instead of the notch/rib arrangement, a screw threaded engagement is utilized to attach retractor housing 118 to sleeve 102.

Figure 6:
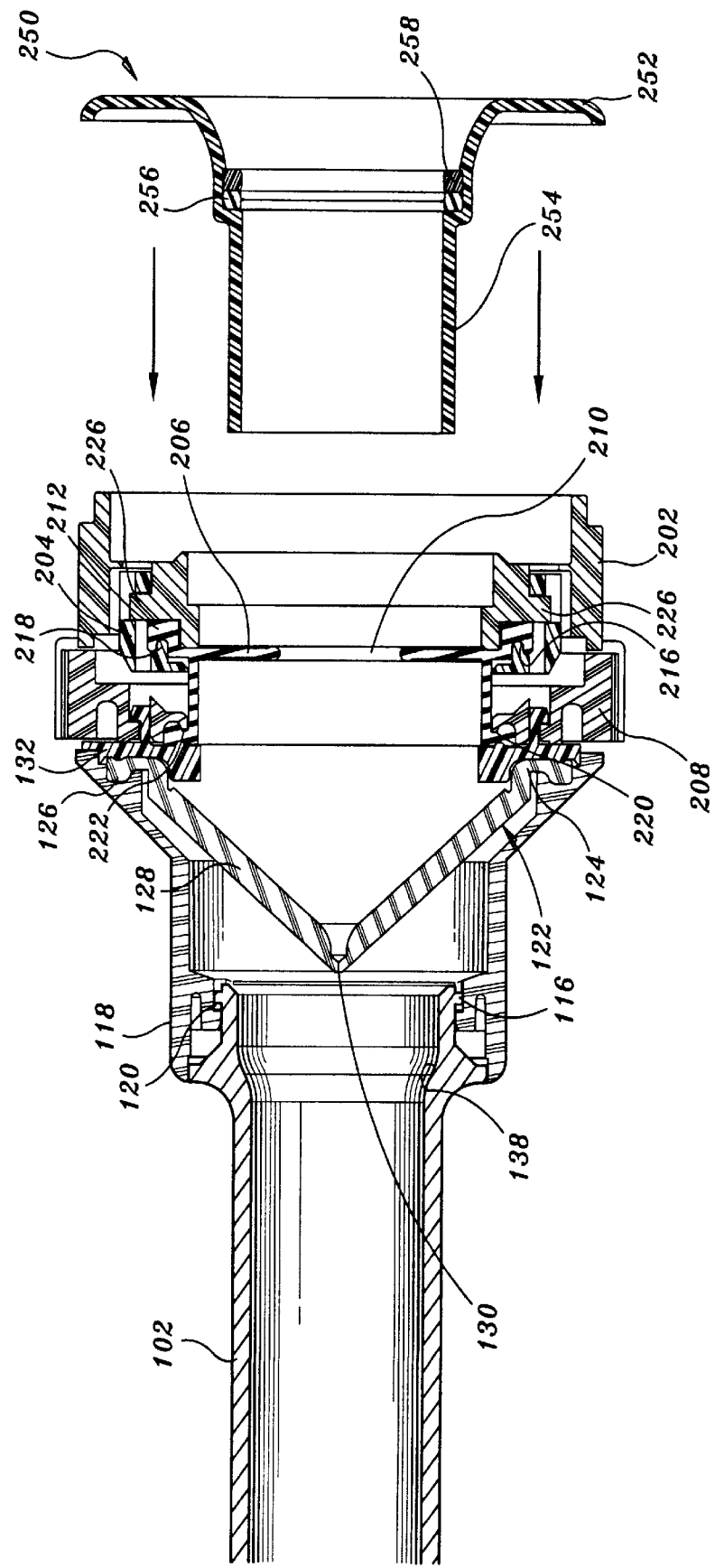
FIG. 6 is an enlarged cross-sectional view of the proximal end of the surgical retractor and mounted valve assembly illustrating the converter prior to insertion within the valve assembly.
Figure 7A:
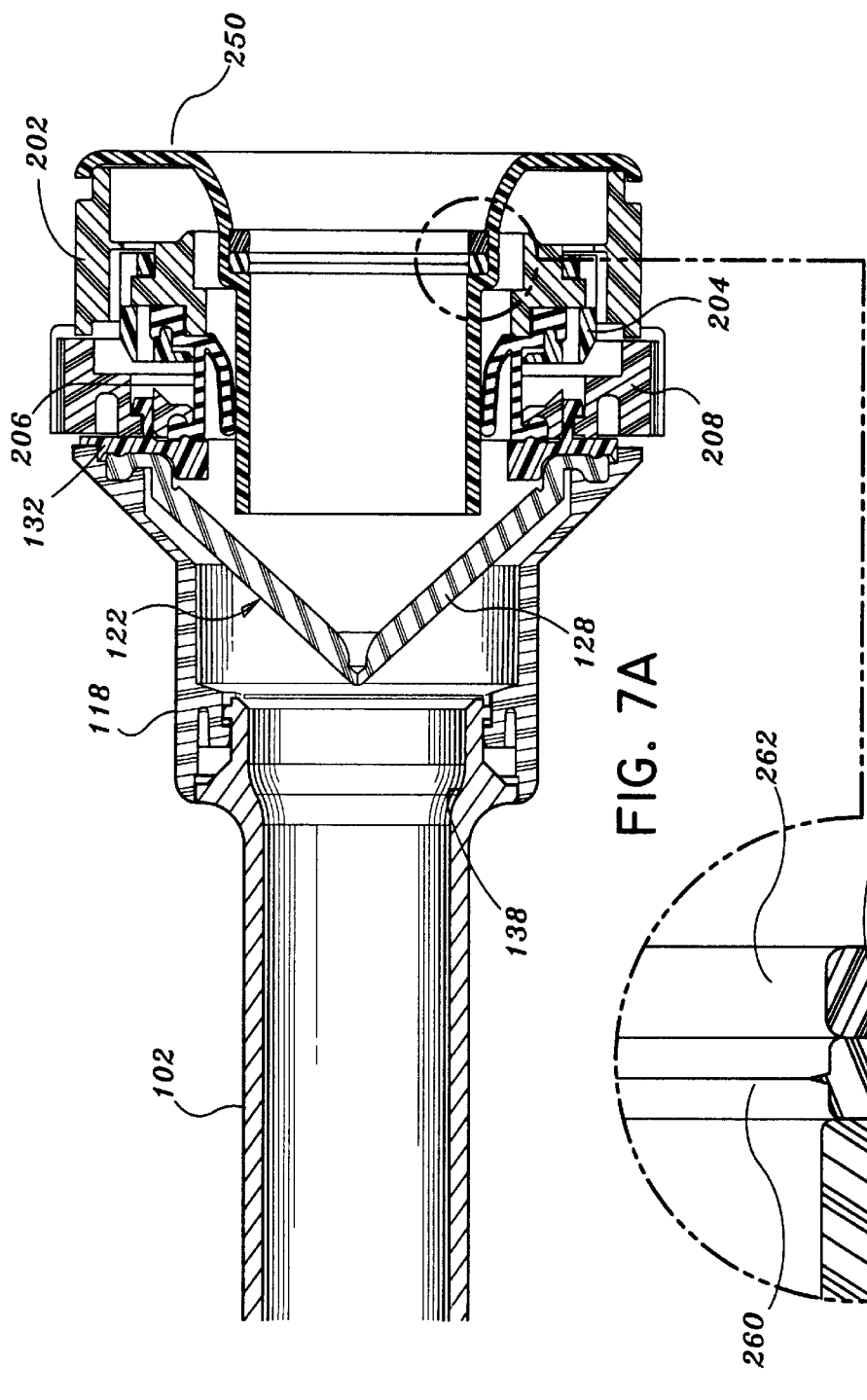
FIG. 7A is a view similar to the view of FIG. 6 with the converter inserted within the valve assembly.

With reference to FIGS. 4 and 6–7, a seal 122 fabricated from a resilient material, e.g., rubber, is positioned within the interior of retractor housing 118. Seal 122 includes a circumferential flange portion 124 which rests on a correspondingly dimensioned circumferential ledge 126 within retractor housing 118. Seal 122 generally defines a duck bill shape having two planar tapering portions 128 which intersect at their distal ends to define abutment face or slit 130. Abutment slit 130 permits passage of the elongated object through the seal 122, but, in the absence of an instrument, and particularly when retractor 100 is inserted into an insufflated body cavity, abutment slit 130 forms a gas-tight seal that isolates the insufflated cavity from the ambient surroundings. Seal 122 may include at least one, preferably two, reinforcing ribs (not shown) to stabilize the seal. The ribs are preferably positioned to engage the instrument to guide the instrument through slit 130 and prevent piercing of the seal 122 by the tip of the instrument.

Retractor housing 118 also includes a stabilizing plate 132 (FIG. 4) which is positioned against the flange portion 124 of seal 122 to provide support for the seal during introduction and withdrawal of an elongated instrument. Stabilizing plate 132 includes two diametrically opposed extensions 134 which are received within the correspondingly dimensioned leg portions 118a of the retractor housing 118. In the preferred embodiment, stabilizing plate 132 is securely attached to retractor housing 118 at contact points along the extensions of the respective components by spot welding, adhesives or the like. Stabilizing plate 132 also includes a partial external annular rib or thread (not shown) adjacent its proximal end.

A stop cock valve 136 may optionally be incorporated as part of the retractor housing 118 to permit the passage of insufflation gases through the sleeve 102 and into the body cavity. Insufflation gases can continually be introduced during the procedure to maintain the inflated condition of the peritoneal cavity.

Valve Assembly

Referring now to FIGS. 4–7, the valve assembly will be discussed in detail. Valve assembly 200 is intended to sealingly receive ark elongated object inserted therethrough. Valve assembly includes end cap 202, seal retainer ring 204, seal element 206 and seal housing 208. These components are assembled to form a single unit which is adapted for releasable mounting the valve assembly to retractor housing 118 of retractor 100.

Seal element 206 is a conventional flat seal having aperture 210 and first and second flanges 212, 214 at its respective ends. Flange 212 is positioned between corresponding peripheral structure of end cap 202 and seal retainer ring 204 and retained therein in the assembled condition of valve assembly 200 (FIG. 6). In particular, flange 212 defines peripheral recess 216 which receives correspondingly dimensioned peripheral rib 218 of seal retainer ring 204 to mount the flange 212. Similarly, flange 214 includes peripheral recess 220 which receives correspondingly dimensioned peripheral rib 222 of seal housing 208 to mount the flange 214. Seal element 206 is preferably fabricated from an elastic fabric material such as polyisoprene, and is capable of deforming to receive instrumentation of various sizes through aperture 210 and form a substantially fluid-tight seal about the instrument.

Seal retainer ring 204 is mounted to end cap 202 through cooperative engagement of peripheral grooves 224 of the retainer ring 204 and corresponding locking lugs 226 within the interior of the end cap 202 (FIGS. 4 and 6). The assembled seal retainer ring 204 and end cap 202 are mounted to seal housing 208 through cooperative engagement of mounting projections 228 of the end cap 202 and mounting apertures 230 of the seal housing 208 (FIG. 4). The assembled valve assembly 200 is mountable to retractor 100 as follows: Seal housing 208 includes a distal end face having peripheral groove 232 and two opposed rib portions 234 extending radially inwardly adjacent the groove 232. Groove 232 and rib portions 234 assist in mounting valve assembly 200 to housing 118. In particular, the partial thread (not shown) of stabilizing plate 132 is received within peripheral groove 232 of seal housing 208 and the entire assembly is rotated causing engagement of the radially inwardly projecting rib portions 234 adjacent the groove 232 with the partial annular thread of the plate to releasably lock the valve assembly 200 to the housing 118. As indicated above, stabilizing plate 132 is fixed to housing 118. Other means for detachably connecting valve assembly 200 to housing 118 can be readily determined by one skilled in the art such as screw threads, adhesives, bayonet locking and the like.

Another valve assembly suitable for use with retractor 100 is disclosed in U.S. Pat. No. 5,603,702 to Smith et al, the contents of which are incorporated herein by reference.

It should be appreciated that valve assembly 200 can be packaged pre-attached to retractor 100 or alternatively be formed as an integral unit. As another alternative, the valve assembly 200 can be packaged as a separate unit and attached to the retractor 100 by the user.

Converter

Figure 7B:
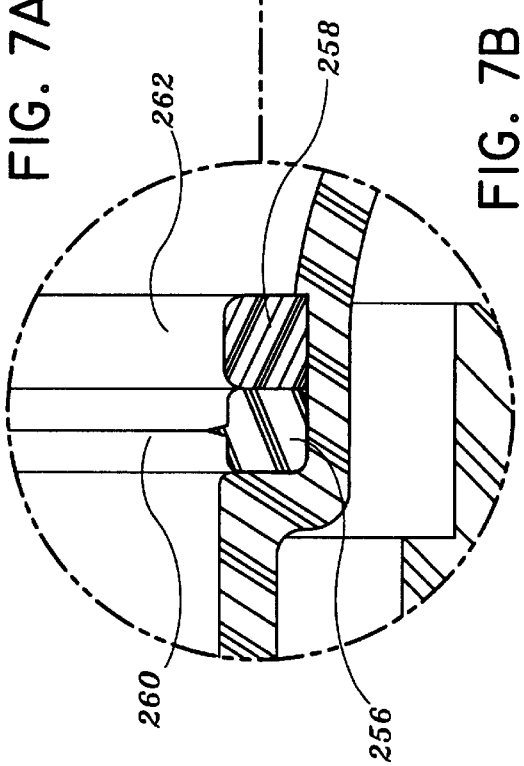
FIG. 7B is an isolated view illustrating mounting of the seal rings in the converter.
Figure 8:
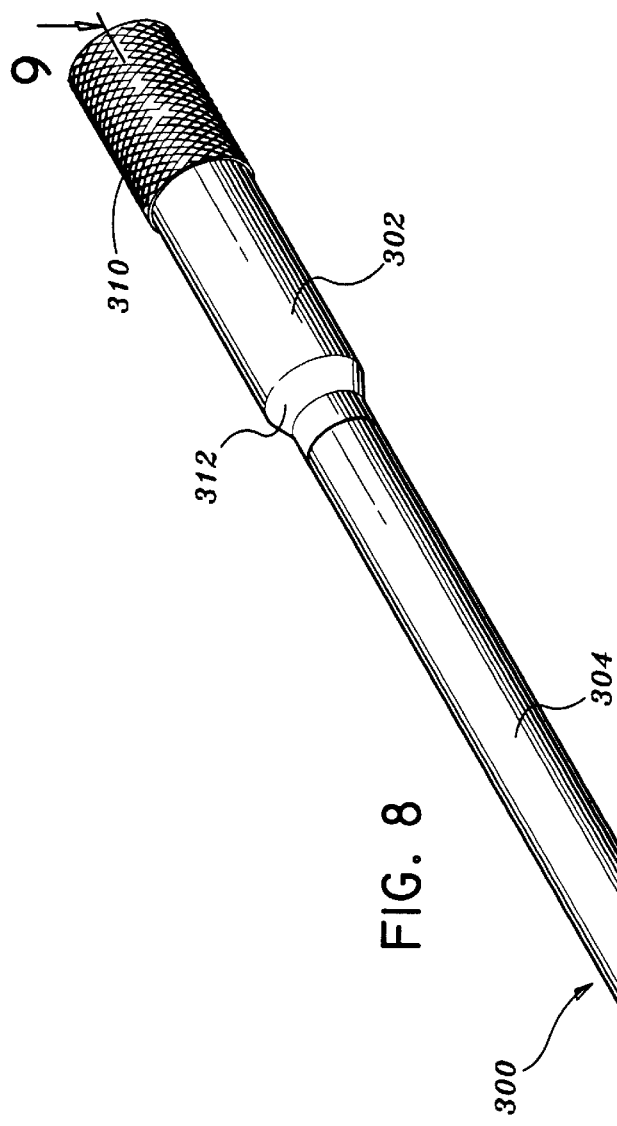
FIG. 8 is a perspective view of the impactor instrument.
Figure 9:
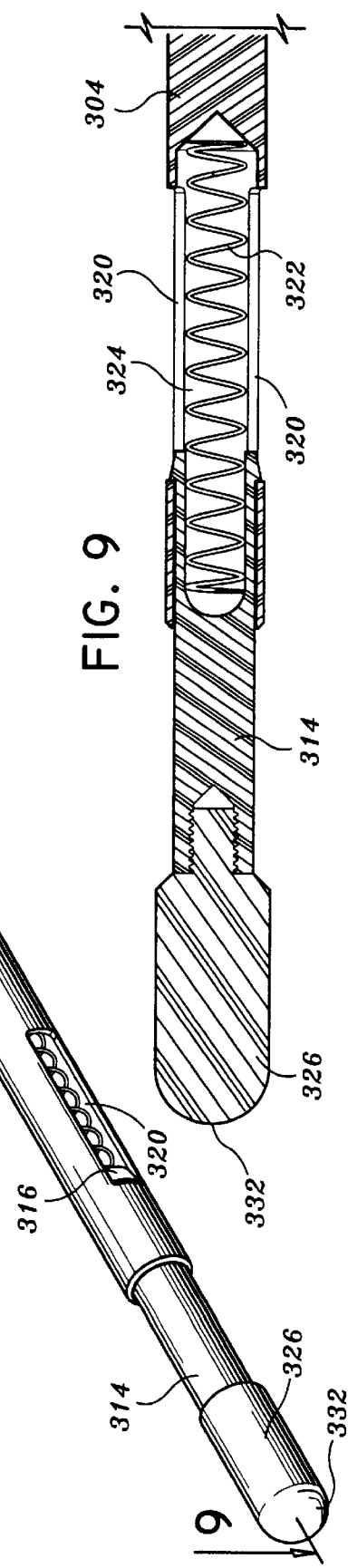
FIG. 9 is a cross-sectional view taken along the lines 9—9 of FIG. 8.

Referring to FIGS. 4, 6 and 7A–7B, a converter 250 may be used in conjunction with valve assembly 200. Converter 250 enables the use of various diameter instruments while maintaining a fluid tight seal about the instrument. Converter 250 also protects seal element 206 by precluding the distal end of the inserted instrument from engaging any portion of seal element 206 during use. Converter 250 includes proximal flange 252 dimensioned to be grasped by the user and distal introducing portion 254. Converter 250 further includes first and second O-rings 256, 258 mounted in side-by-side relation within corresponding recesses 260, 262 of the converter 250. (FIG. 7B)

Converter 250 is mounted to valve assembly 200 by inserting introducing portion 254 with the assembled valve assembly 200. Upon insertion through aperture 210 of seal element 206, the portions of the seal defining the aperture 210 stretch and form a fluid tight seal about the distal introducing portion 254. Thereafter, instruments are introduced through converter 250 whereby upon insertion O rings 256, 258 cooperate to form a fluid tight seal about the instrument. Converter 250 may be of various sizes or diameters to accommodate various diameter instruments inserted therethrough. The different sized converters 250 may be readily exchanged by simple withdrawal and insertion within valve assembly 200. Similar commercially available converters (i.e. reducer sleeves) are available from Stryker Endoscopy, Aesculap and Core Dynamics.

It is to be appreciated that valve assembly 200 can be used without converter 250 whereby seal element 206 forms a seal about the inserted instrument.

Impactor Instrument

With reference now to FIGS. 8–11, impactor instrument 300 will be discussed. Impactor 300 is intended to facilitate the insertion of retractor 100 in the desired intervertebral space. As depicted, impactor 300 includes handle 302 and elongated portion 304 connected to the handle and extending distally therefrom. In a preferred arrangement, handle 302 defines an internal threaded bore 306 which threadably engages a proximal threaded portion 308 of elongated portion 304. Other means For connecting handle 302 and elongated portion 304 are envisioned as well. It is also envisioned that handle 302 and elongated portion 304 may be formed as a single unit. Handle 302 defines a knurled outer surface 310 to facilitate its handling. The cross-sectional dimension of handle 302 decreases at its distal end to define a sloped abutment surface 312, the significance of which will be discussed in greater detail hereinbelow.

Impactor instrument 300 includes extension member 314 which is mounted at the distal end of elongated member 304. Extension member 314 has bifurcated portions 316 at its proximal end which are received within the axial bore of elongated member 304. Bifurcated portions 316 include radial tabs 318 which are respectively received within correspondingly dimensioned axial slots 320 of the elongated member 304 to mount the extension member 314 to the elongated member 304. Extension member 314 is mounted for limited reciprocal axial movement relative to elongated member 304 through traversing movement of tabs 318 of extension member 314 through axial slots 320 of the elongated member. A coil spring 322 received within a partial longitudinal bore 324 (FIG. 9) of extension member 314 normally biases the extension member 314 to a distal-most position.

An impactor head 326 is mounted to the distal end of extension member 314. In a preferred arrangement, impactor head 326 has a threaded proximal end portion 328 of reduced cross-section that is received within an internal threaded bore 330 of extension member 314 to mount the two components. Impactor head 326 defines a rounded end 332 which is advantageously dimensioned to remove tissue from the operative site. The cross-sectional dimension of impactor head 326 is preferably greater than the size or height of the intervertebral space to prevent entry thereof into the space. Impactor head 326 is also dimensioned to span the interior area of retractor sleeve 102 thus preventing body fluids from entering the retractor 100 during insertion.

Figure 12:
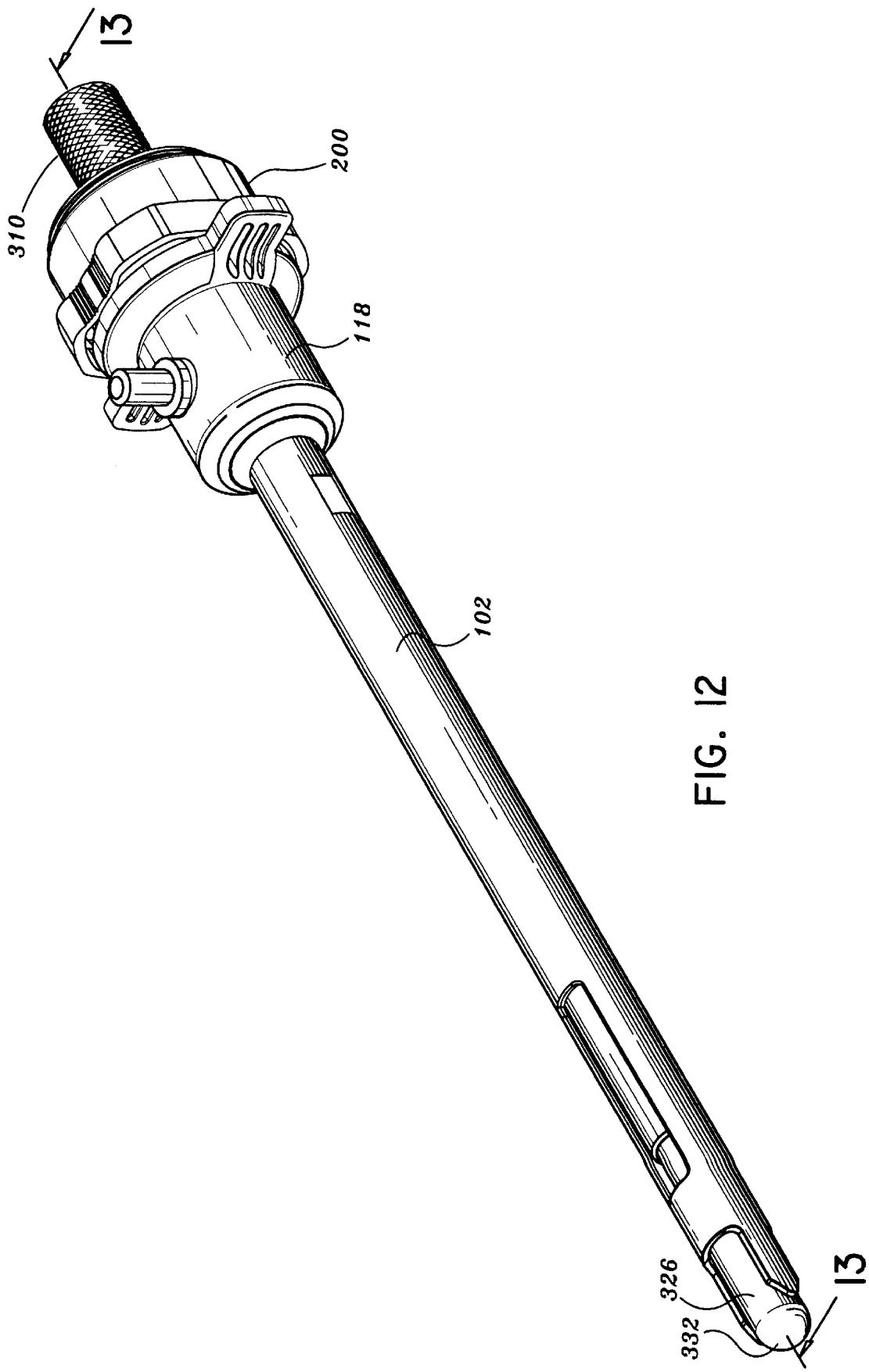
FIG. 12 is a perspective view of the surgical retractor and mounted valve assembly with the impactor instrument mounted therewithin.
Figure 17:
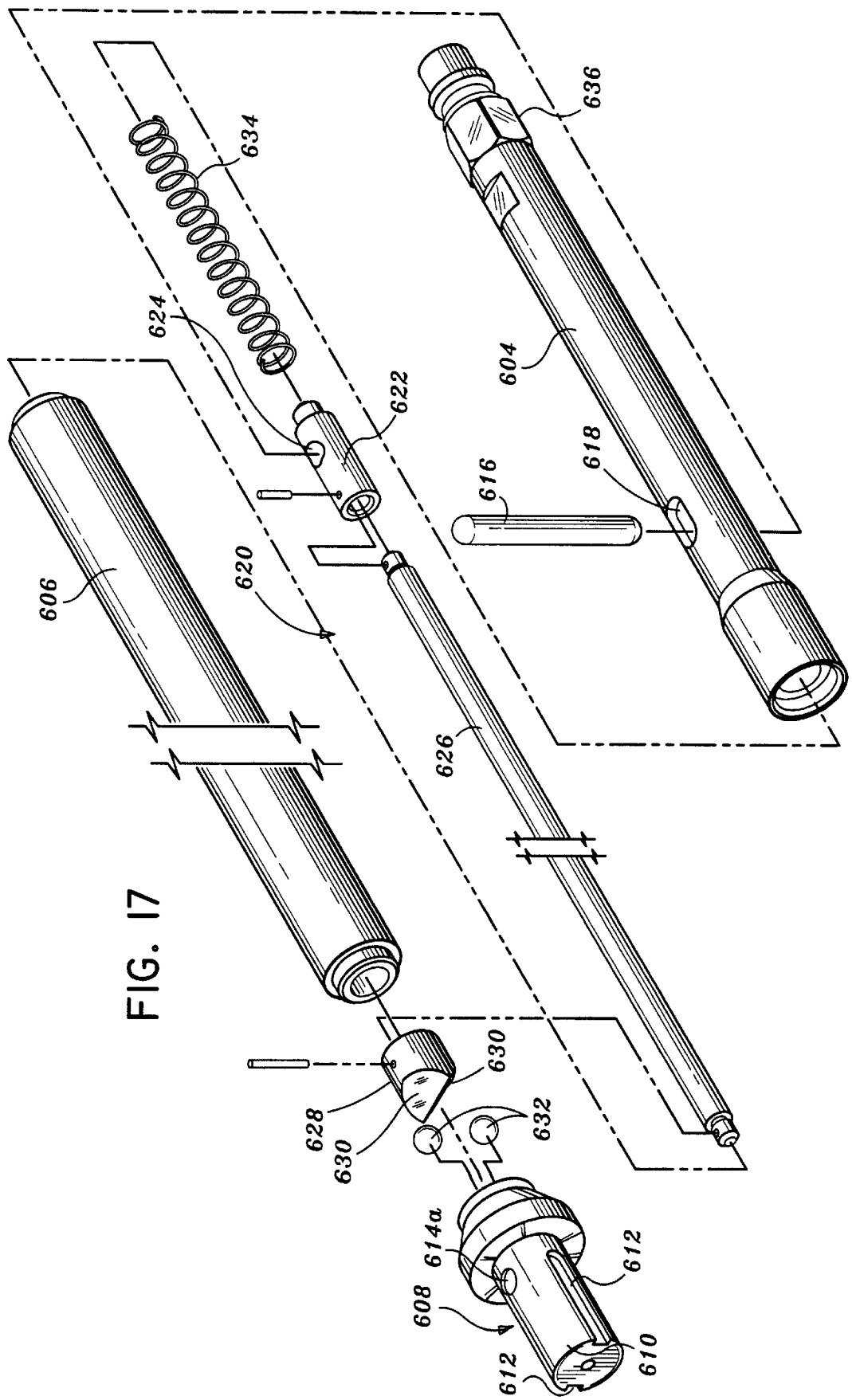
FIG. 17 is a perspective view with parts separated of the implant insertion instrument.

FIGS. 12–14 depict impactor instrument 300 positioned within retractor 100, mounted valve assembly 200 and converter 250. Upon insertion of impactor instrument 300 within valve assembly 200, O-ring seals 256, 258 form a fluid tight seal about the instrument. Continued passage of impactor instrument 300 through retractor 200 opens housing valve 122 to also permit passage of the instrument. The O-rings 256, 258 of valve assembly 200 sealingly engage handle 302 to form a substantially fluid-tight seal about impactor instrument 300 thus preventing egress of insufflation gases. As best depicted in FIGS. 13–14, in the assembled position of impactor instrument 300 within retractor 100, abutment surface 312 defined on handle 302 of impactor instrument 300 engages inner sloped surface 138 (see also FIG. 6) of retractor 100. With this arrangement, distal movement of the impactor instrument 300 will also drive retractor 100 distally.

Drill Instrument

Referring again to FIG. 1, drill instrument 400 is also disclosed in the '379 application. Drill instrument 400 includes drill shaft 402, extension shaft 404 and drill bit 406 mounted at the distal end of the drill shaft. Extension shaft 404 has first and second collars 408, 410 which cooperate to control the depth of penetration of drill shaft 402 and drill bit 406 into the adjacent vertebrae. Drill shaft 402 includes a hexagonal-shaped head 412 at its proximal end to mount T-handle 800.

Tap Instrument

Referring still to FIG. 1, tap instrument 500 will be discussed. Tap instrument 500 is also disclosed in the '379 application. Tap instrument 500 is utilized for forming an internal thread within the drilled bore formed by the drill instrument 400. Tap instrument 500 includes elongated member 502 having hex head 504 at its proximal end to engage T-shaped handle 800. Tap instrument 500 further includes distal tapping threaded portion 506. Distal tapping portion 506 includes a plurality of conveyance channels (one is shown) 508 extending longitudinally through the cutting thread. Each conveyance channel 508 has a directional component parallel to the longitudinal axis and a directional component transverse to the longitudinal axis. Each conveyance, channel 508 encompasses approximately an arc of about ⅓ the outer circumference of the tapping portion 506. Conveyance channels 508 are each dimensioned to receive bone material deburred by the cutting edges during the tapping procedure and to continually transmit the bone material proximally through the channel to avoid undesired material build up at the tapping site. In this manner, tapping instrument 500 may be used to completely tap the internal thread within the bore without interruption of the tapping procedure.

Insertion Instrument

Referring now to FIGS. 15–18, implant insertion instrument 600 will be discussed in detail. Implant insertion instrument 600 includes outer elongated sleeve 602 having proximal portion 604 and distal portion 606 which is connected to the proximal portion 604 by conventional means appreciated by one skilled in the art. It is also envisioned that elongated sleeve 602 may be one unitary component as well. Elongated sleeve 602 defines a longitudinal bore extending therethrough. The distal end of elongated sleeve 602 has an implant mounting collar 608 connected thereto. Implant mounting collar 608 includes cylindrical mounting portion 610 which is appropriately dimensioned to be received within the internal cavity of fusion implant 700. Mounting portion 610 has first and second diametrically opposed grooves 612 extending in a longitudinal direction and transverse channel 614 terminating in diametrically opposed radial openings 614a.

A deployment mechanism is incorporated within implant insertion instrument 600 for deploying fusion implant 700. The deployment mechanism includes manually actuated lever 616 which extends through diametrically opposed slots 618 in elongated sleeve 602, and drive member 620 operatively connected to the manually actuated lever 616. Drive member 620 includes drive collar 622 defining aperture 624 for reception of manually actuated lever 616, and drive rod 626 connected to the drive collar 622 through a corresponding pin and slot arrangement as shown. A cam member 628 is mounted to the distal end of drive rod 626 also through a pin and slot arrangement. Cam member 628 defines first and second inclined camming surfaces 630 which respectively engage mounting balls 632 disposed within transverse channel 614 of implant mounting collar 608. Cam member 628 is movable through respective movement of the deployment mechanism between a release position to enable disengagement of the implant 700 from insertion instrument 600 and an engaged position to retain the implant 700 on implant mounting collar 608.

Figure 19:
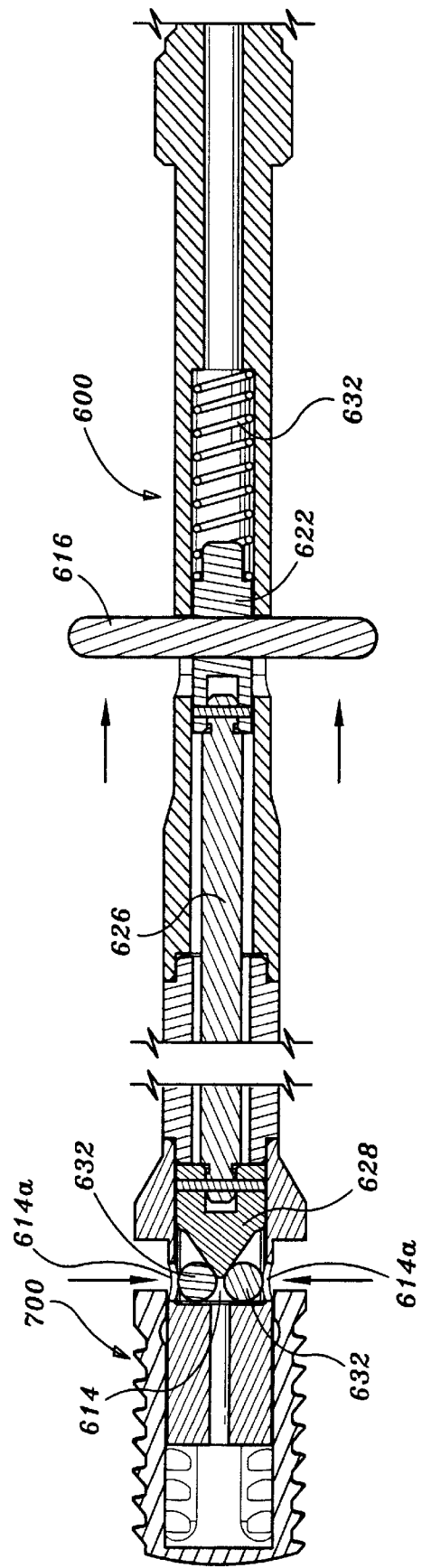
FIG. 19 is a view similar to the view of FIG. 18 illustrating the insertion instrument in a release position permitting release of the fusion implant.

FIGS. 18–19 depict the deployment mechanism of implant insertion instrument 600 in the engaged and disengaged positions respectively. In the engaged position, manually actuated lever 616 is in a distalmost position corresponding to an advanced position of drive member 626 and cam member 628 whereby mounting balls 632 are biased outwardly at least partially protruding beyond openings 614a and in engagement with implant 700 thereby positively fixing the implant to the instrument as depicted in FIG. 18. In the disengaged position, manually actuated lever 616 and, thus, drive member 620 are in a proximalmost position permitting mounting balls 632 to be retracted within transverse channel 614 of implant mounting collar 608 thereby enabling implant 700 to be released from mounting collar 608. The deployment mechanism is normally biased to the engaged position by coil spring 634 which engages the proximal end of drive collar 622. Implant insertion instrument 600 includes proximal hex head 636 for coupling to T-handle 800.

Fusion Implant

Referring again to FIG. 1, implant 700 will be described. Implant 700 is uniquely designed for use in spinal fusion procedures. This implant 700 is generally disclosed in U.S. Pat. No. 5,026,373 to Ray, the contents of which have been previously incorporated herein by reference, and is commonly referred to as a "fusion cage". Implant or fusion cage 700 includes a cylindrical cage body 702 having an internal cavity or hole for accommodating bone-growth inducing substances. One end of cage body 702 is closed and defines a rounded or bull-nosed configuration to facilitate insertion of the fusion cage relative to one or more bony structures. The other end defines an opening which communicates with the internal cavity. The outer surface of the cage body 702 includes a single continuous thread (preferably V-shaped) having a plurality of raised turns, with valleys defined between adjacent turns.

A plurality of perforations are disposed within the thread and extend through the outer surface of the cage body 702 to provide direct communication between the outer surface and internal cavity. The perforations permit immediate contact between the bone growth inducing substances within the inner cavity and the bone structure when the cage body 702 is mated to the bone structure, e.g., adjacent vertebrae. An end cap (not shown) may be mountable to the open end of cage body 702 to enclose the bone-growth inducing substances within the interior cavity.

With reference to FIG. 20, which is a cross-sectional view taken along the lines 20—20 of FIG. 18, and to FIG. 20A which is a perspective view with a portion cutaway of the implant or cage 700, cage body 702 further includes longitudinal rails 704 extending within the internal cavity and a pair of diametrically opposed inner arcuate recesses 706 (FIGS. 18 and 20A) disposed proximate the proximal end of the implant 700. Longitudinal rails 704 are received within longitudinal grooves 612 of mounting collar 608 when the implant 700 is mounted onto the collar 608, thus, rotatably fixing the implant 700 relative to insertion instrument 600. Arcuate inner recesses 706 of implant 700 receive portions of mounting balls 632 when the deployment mechanism is in the engaged position of FIG. 18, thus, positively securing the implant 700 on the insertion instrument 600.

T-Handle

T-shaped handle 800 includes mounting portion 802 defining hexagonal-shaped recess 804 which receives the corresponding structure of drill instrument 400, tap instrument 500 and implant insertion instrument 600.

Operation of Surgical Instrumentation

The use of the instrumentation in conjunction with the insertion of fusion implant 700 into an intervertebral space defined between adjacent vertebrae will be described. The subsequent description will be particularly focused on a laparoscopic anterior procedure.

The peritoneal cavity is insufflated with insufflation gases which are introduced through a peritoneum needle of an insufflation apparatus, thus, distending the peritoneal lining and providing enhanced access therein. Thereafter, an incision is made in the abdominal cavity and retractor 100 having valve assembly 200 mounted thereto is positioned within the incision.

Figure 21:
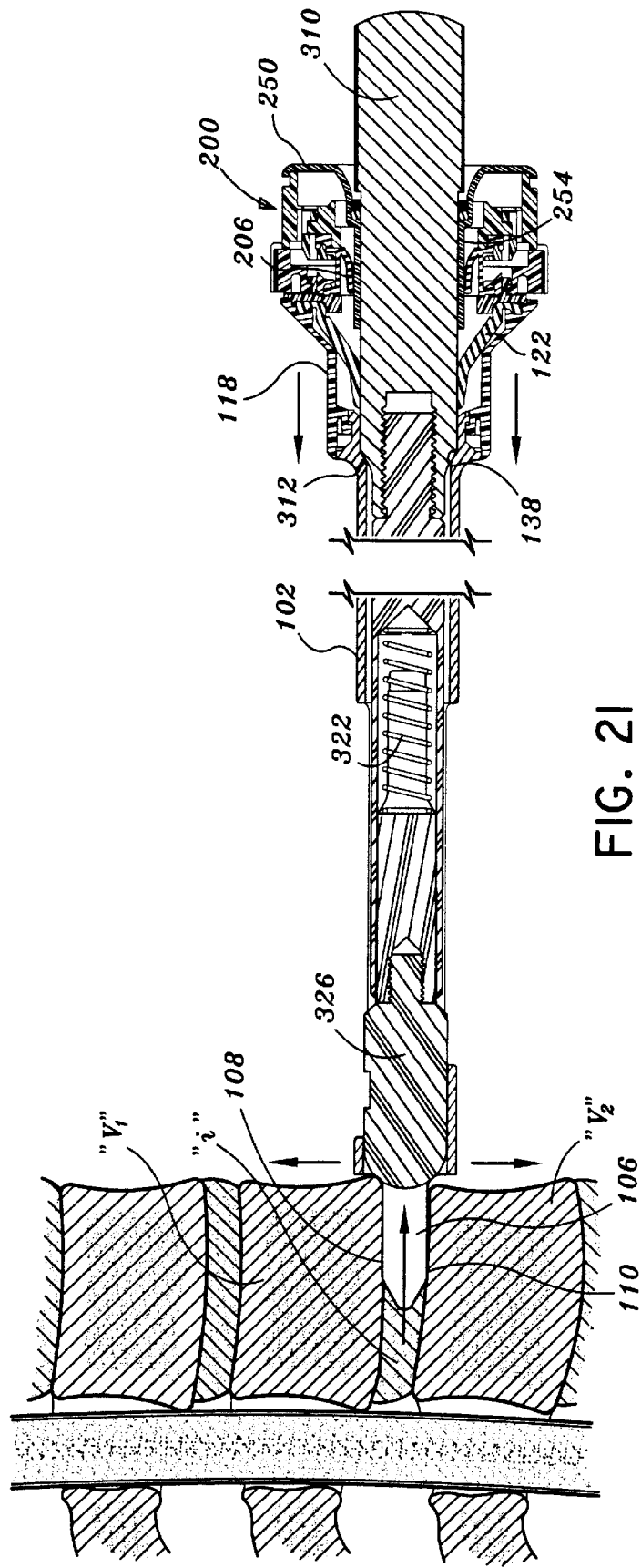
FIG. 21 is a side cross-sectional view illustrating mounting of the surgical retractor within the intervertebral space defined between adjacent vertebrae through a laparoscopic approach and with the assistance of the impactor instrument positioned within the retractor.

The intervertebral space is accessed utilizing appropriate retractors, e.g., laminal retractors, dural extractors which may be introduced through retractor 100 or other strategically placed cannulas accessing the peritoneal cavity to expose the anterior vertebral surface. With reference to FIG. 21, impactor instrument 300 is inserted through converter 250, valve assembly 200 and within retractor sleeve 102. Seals 256, 258 of converter 250 form a fluid-tight seal about instrument 300 in the manner discussed above. Seal element 206 sealingly engages introducing portion 254 of converter 250. Impactor instrument 300 is fully advanced within retractor 100 to a position where abutment surface 312 of handle 302 engages inner sloped surface 138 of retractor sleeve 102. Thereafter, retractor 100 is manipulated to align retractor arms 106 within the desired intervertebral space "i" defined between adjacent vertebrae "$V_1$, $V_2$". Retractor arms 106 are advanced into the intervertebral space "i" whereby first and second supporting surface 108, 110 of each retractor arm 106 respectively engage the opposed vertebral bodies "$V_1$, $V_2$". During insertion, impactor instrument 300 is driven distally, by e.g., impacting handle 302 with a standard mallet, which thereby drives retractor 100 within the adjacent vertebrae "$V_1$, $V_2$" through cooperation of abutment surface 312 of the impactor instrument 300 and sloped surface 138 of retractor sleeve 102. During insertion, impactor head 326 of impactor instrument 300 removes tissue from the operative site and also prevents entry of body fluids within the interior of retractor sleeve 102. Impactor head 326 also retracts against the bias of coil spring 322 upon engagement with the anterior surface of the vertebrae "$V_1$, $V_2$" so as to not penetrate the intervertebral space "i".

Figure 22:
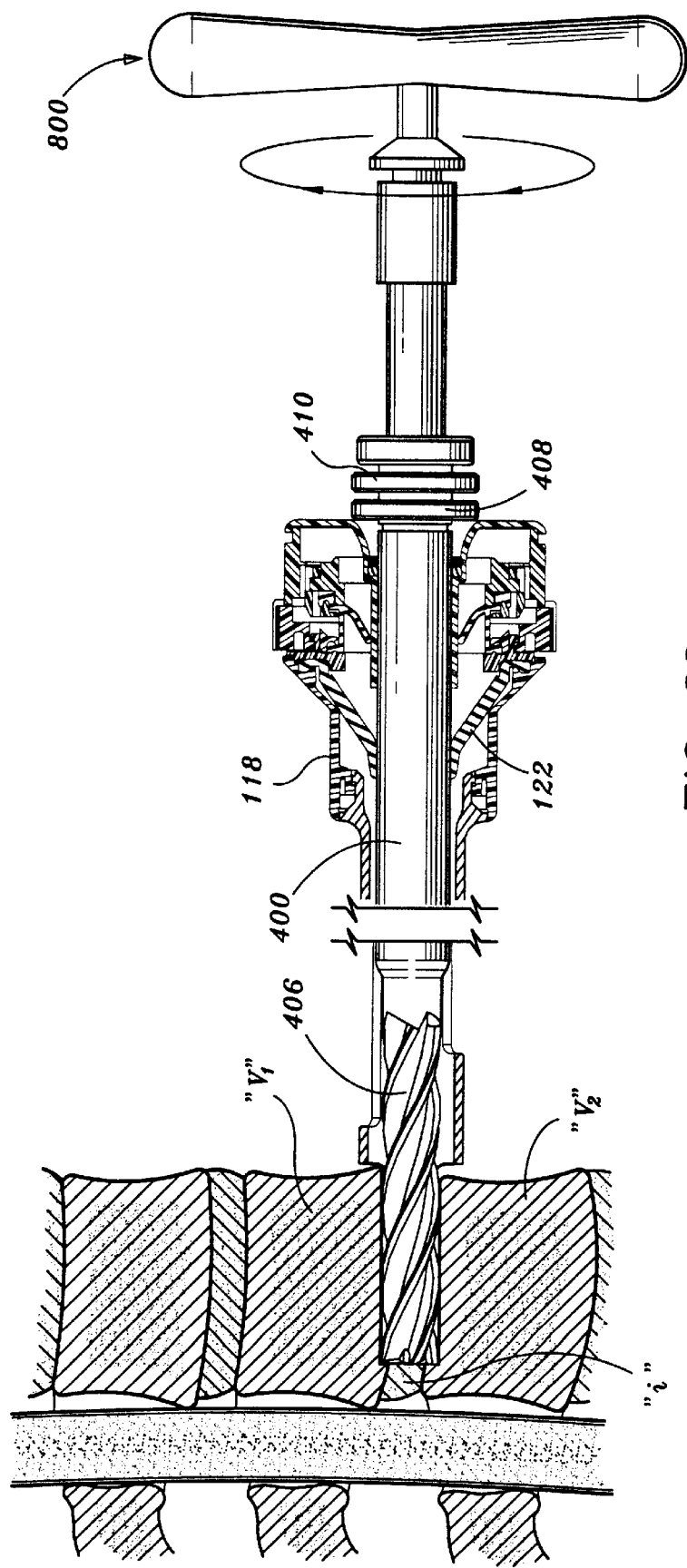
FIG. 22 is a view similar to the view of FIG. 21 illustrating insertion of the drill instrument through the surgical retractor to drill a bore between the adjacent vertebrae.

Referring now to FIG. 22, with retractor arms 106 of retractor 100 in their appropriate position within the intervertebral space "i", impactor instrument 300 is removed from retractor 100 and valve assembly 200. During removal, valve 122 of retractor housing 118 assumes its closed position preventing egress of insufflation gases from the peritoneal cavity. Thereafter, drill instrument 400 is introduced through converter 250, valve assembly 200 and retractor 100. Upon insertion, a seal is formed about drill instrument 200 in a manner similar to that discussed above in connection with impactor instrument 300.

The cutting depth of drilling instrument is adjusted as desired (i.e., to correspond to the length of the fusion implant) by adjusting collars 408, 410. This may be done prior to the insertion within retractor 100. With the T-handle 800 mounted to surgical drill instrument 400, the instrument is introduced into valve assembly 200 and the axial bore of retractor 100 and advanced to contact the posterior surface of the vertebral bodies, "$v_1 \, v_2$". Drill 400 is advanced into the intervertebral space "i" by rotating T-handle 800 such that drill bit 406 shears the soft tissue and cuts the bone of the, adjacent vertebrae "$v_1 \, v_2$" thereby forming a bore which extends into the adjacent vertebrae "$v_1 \, v_2$". Drill 400 is then removed from retractor 100.

Figure 23:
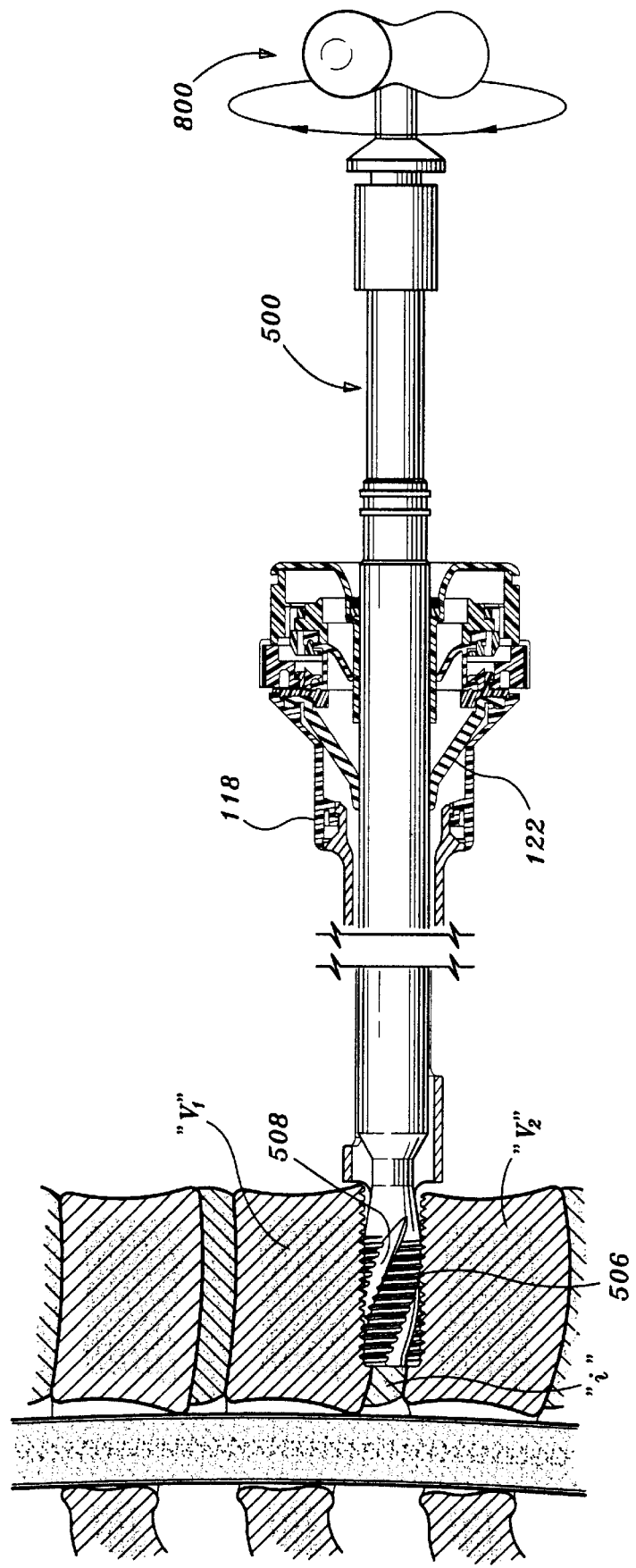
FIG. 23 is a view similar to the view of FIG. 22 illustrating insertion of the tap instrument within the retractor for tapping the bore formed by the drill instrument.

Referring now to FIG. 23, tap instrument 500 is selected and attached to the T-handle 800. Tap instrument 500 is inserted into converter 250, valve assembly 200 and retractor 100 and positioned adjacent the drilled bore formed in the adjacent vertebrae "$v_1 \, v_2$" by the surgical drill 400. With retractor 100 as a direct guide, T-handle 800 is rotated in the direction of the directional arrow of FIG. 23 while simultaneously applying sufficient downward pressure on the T-handle to advance the tap instrument 500 and promote even purchase into the endplates. Upon advancement of the tap instrument 500, the deburred bone chips collect within conveyance channel 508 of tapping head 506, and are conveyed proximally during rotational movement of the tapping head 506 away from the tapping site. Tap instrument 500 is advanced into the bone until the desired depth has been achieved, which occurs when the distal end of tapping head 508 "bottoms out" on the bone. When tap instrument 500 reaches the appropriate depth, the tap instrument 500 is rotated via T-handle 800 in an opposite direction to back the instrument out of the bone. It is to be appreciated that in procedures where a self-tapping implant is utilized the tapping of the bore with tap instrument 500 is not necessary.

Figure 24:
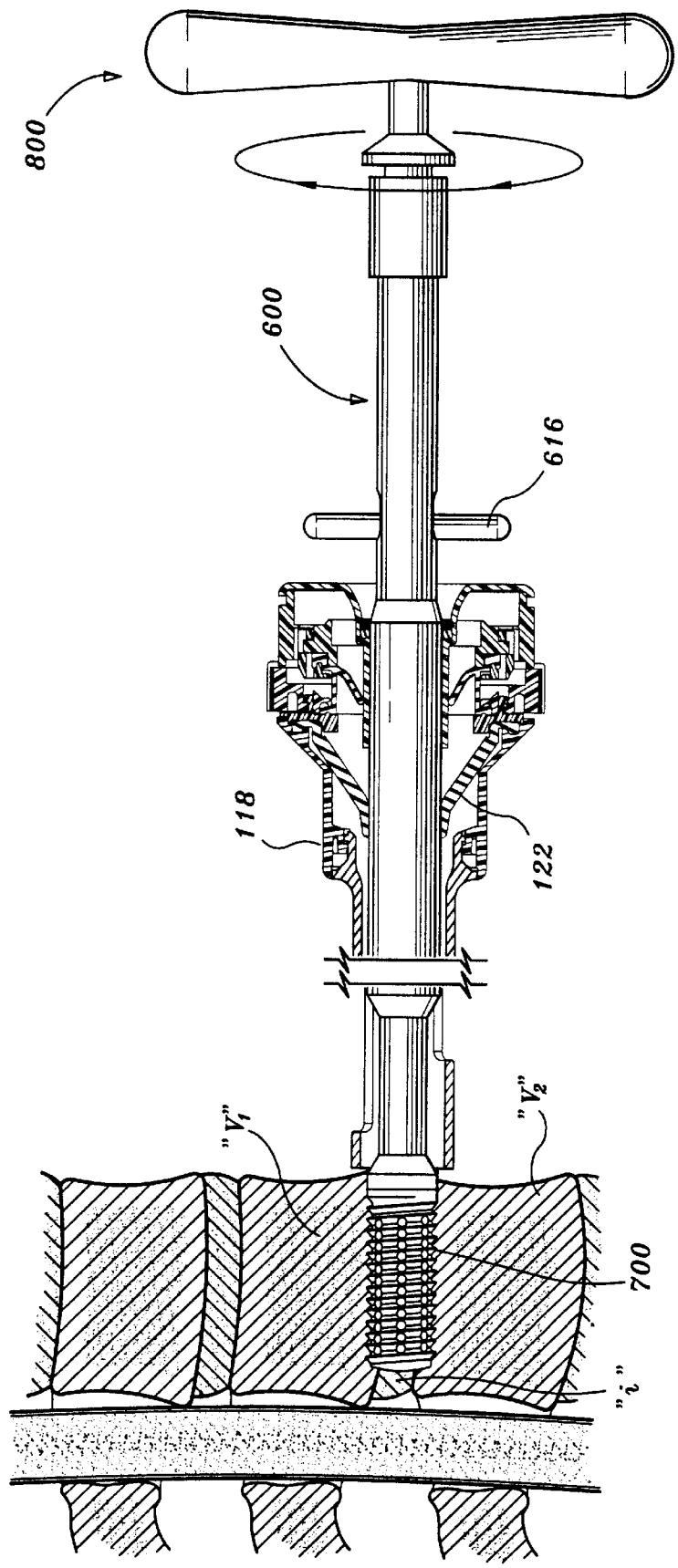
FIG. 24 is a view similar to the view of FIG. 23 illustrating insertion of the implant insertion instrument with mounted fusion implant within the retractor to mount the implant within the tapped bore.

With reference now to FIG. 24, attention is focused on the insertion of fusion implant 700. Cage body 702 is mounted onto insertion instrument 400 by positioning the cage body 702 onto mounting portion 408 of the instrument to permit mounting ball 632 to engage one of the apertures of the implant 700. Initially, insertion instrument 600 is in the position of FIG. 18 such that mounting balls 632 are biased outwardly into engagement with recesses 706 of the implant 700. This assembly is attached to T-handle 800. Insertion instrument 400 with mounted cage body 702 is inserted into retractor 100 and the cage body 702 is positioned within the tapped bore by rotating insertion instrument 600 in the direction depicted in FIG. 8. Cage body 702 is advanced until it is completely seated with the bore. Thereafter, manually actuated lever 616 of insertion instrument 600 is moved in the direction of FIG. 19 thereby retracting drive rod 626 and cam member 628 to permit mounting balls 632 to move out of engagement with implant 700. Upon release of implant 700, insertion instrument 600 is removed from retractor 100.

At this point in the procedure, bone growth inducing substances may be harvested from, e.g., the iliac crest, and packed into the cage body 702 of implant 700 until the cage body 702 is completely filled with bone growth inducing substances. An end cap may then be mounted to the cage body 702. Retractor 100 is then removed. Alternatively, cage body 702 can be pre-packed with bone growth inducing substances prior to insertion.

Figure 25:
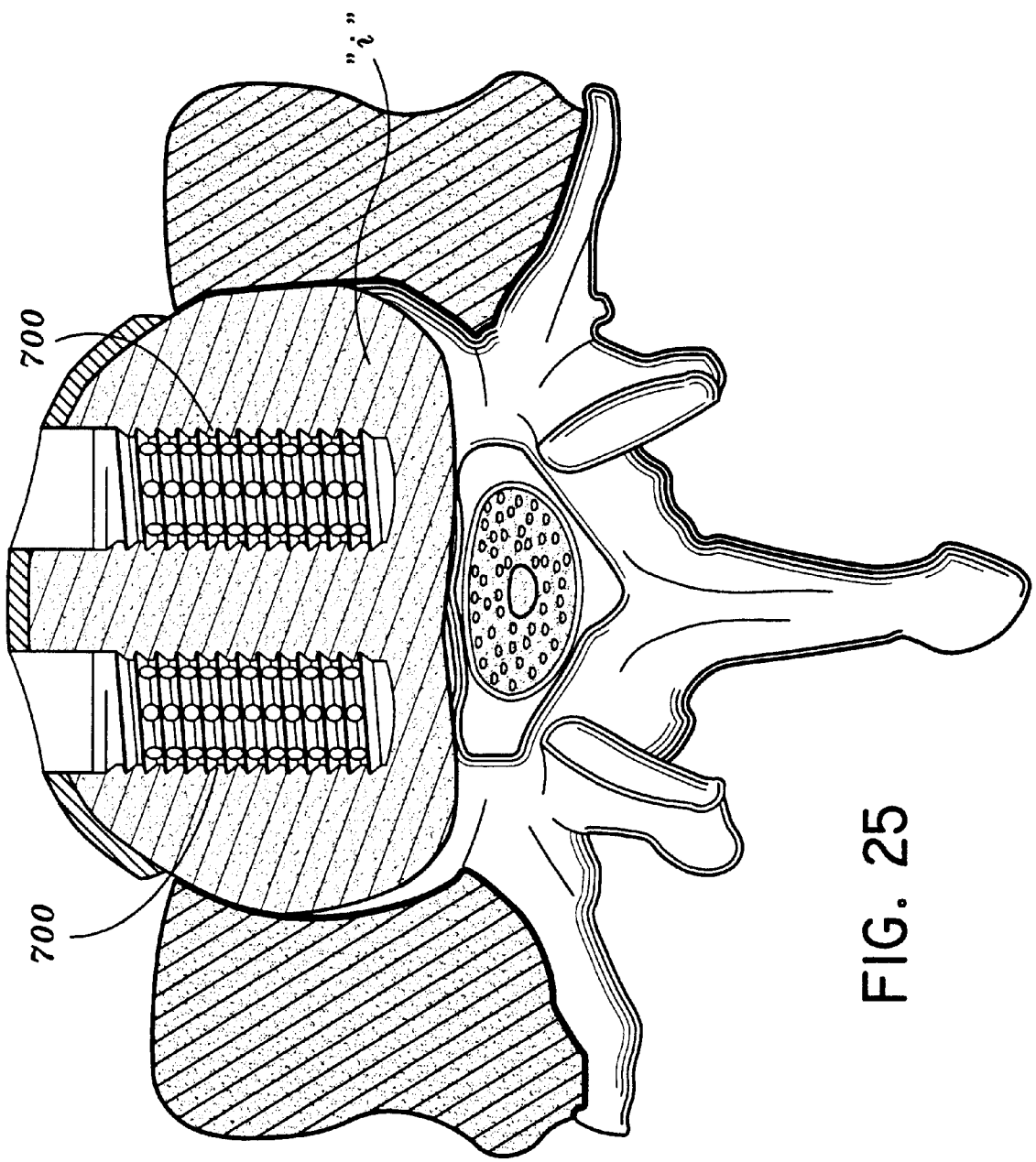
FIG. 25 is a cross-sectional view illustrating the insertion of two implants within the intervertebral space.

FIG. 25 illustrates two lateral fusion implants 700 inserted within the intervertebral space. The second implant 700 may be inserted in the same manner is discussed hereinabove.

Thus, the instrumentation and surgical procedure described herein provide a minimally invasive approach to the insertion of spinal implants for spinal fusion. It is envisioned that the approach will result in less trauma to the patient and minimize recovery time.

Alternate Embodiment of Surgical Retractor

FIGS. 26–28 illustrate an alternate embodiment where the surgical retractor utilizes an impactor end cap or head 140 which is mountable to the proximal end 104 of the surgical retractor 100 in lieu of valve housing 118. In particular, impactor head 140 includes mounting notches 142 which receive mounting ribs 116 of retractor sleeve 102 to releasably mount the impactor head to the retractor sleeve 102. With this arrangement, the impactor head 140 may be impacted with a mallet to drive retractor arms 106 as desired within the intervertebral space "i", thus, precluding the need for impactor instrument 300. Once appropriately positioned, impactor head 140 may be removed and valve housing 118 may be mounted to proximal end 104 of retractor 100 through cooperative engagement of mounting ribs 116 of the retractor 100 with mounting notches of housing 118.

While the above description contains many specifics, these specifics should not be construed as limitations on the scope of the disclosure, but merely as exemplifications of preferred embodiments therefor. For example, several of the instruments described herein e.g., the impactor instrument and implant insertion instrument, can be used in open procedures, as well as the aforedescribed minimally invasive procedures. Those skilled in the art will envision many other possible variations that are within the scope and spirit of the disclosure as defined by the claims appended hereto.

What is claimed is:

1. A laparoscopic surgical retractor assembly for use during a laparoscopic spinal procedure, which comprises:

an elongated sleeve member having proximal and distal end portions and defining a longitudinal opening therethrough, the distal end portion configured for insertion at least partially into an intervertebral space between adjacent opposed vertebrae, the distal end portion including two spaced apart retractor arms having first and second supporting surfaces, each retractor arm defining a dimension between the first and second supporting surfaces sufficient to contact the opposed adjacent vertebrae during insertion thereof to be in supporting engagement therewith; and a valve assembly mounted to the proximal end portion of the elongated sleeve member for substantially sealing the surgical instrument introduced within the longitudinal opening of the sleeve member.

2. The surgical retractor assembly according to claim 1 wherein the valve assembly is releasably mounted to the proximal end portion of the sleeve member.

3. The surgical retractor assembly according to claim 2 wherein the valve assembly includes a valve housing and a valve member mounted to the valve housing and formed of a resilient material and defining an aperture, the aperture being configured and dimensioned such that upon insertion of the surgical instrument into the aperture the resilient material resiliently engages the outer surface of the object in a substantially fluid-tight manner.

4. The surgical retractor assembly according to claim 3, further including a converter, the converter insertable within the aperture of the valve member and having a seal member defining a seal aperture adapted to form a seal about the outer surface of the surgical instrument inserted therethrough.

5. The surgical retractor assembly according to claim 1 the first and second supporting surfaces of each retractor arm are substantially planar.

6. The surgical retractor assembly according to claim 1 further including an elongated impactor instrument positionable within the longitudinal opening of the sleeve member, the impactor instrument utilized to facilitate mounting of the surgical retractor within the adjacent vertebrae.

7. The surgical retractor assembly according to claim 6 wherein the surgical retractor and the impactor instrument include corresponding engaging surfaces such that applying a distal force to the impactor instrument causes, the surgical retractor to be advanced distally within the adjacent vertebrae.

8. The surgical retractor assembly according to claim 7 wherein the impactor instrument includes an elongated member and a distal impactor head configured to prevent entry of fluids within the surgical retractor when positioned within the longitudinal opening of the surgical retractor.

9. The surgical retractor assembly according to claim 8 wherein the impactor head is longitudinally movable relative to the elongated member.

10. The surgical retractor assembly according to claim 9 wherein the impactor head is spring biased distally.

11. The surgical retractor according to claim 1 wherein the dimension between the first and second support surfaces of each retractor arm is at least equal to the height of the intervertebral space.

12. A laparoscopic surgical retractor for use during a laparoscopic procedure, comprising an elongated sleeve member having proximal and distal end portions and defining a longitudinal axis, the sleeve member having a longitudinal opening extending therethrough, the distal end portion including two spaced apart retractor arms having first and second supporting surfaces, the first and second supporting surfaces of each retractor arm being laterally spaced with respect to the longitudinal axis sufficient to distract the opposed tissue portion upon insertion thereof, and a retractor housing mounted to the sleeve member and having a seal member associated therewith adapted to prevent egress of insufflation gases in the absence of a surgical instrument.

13. A surgical retractor according to claim 12 wherein the housing is releasably mounted to the sleeve member.

14. A surgical retractor according to claim 12 further including a valve assembly mounted to the retractor housing, the valve assembly having a valve housing and a valve member mounted to the valve housing and adapted to form a substantially fluid-tight seal about an object inserted therethrough.

15. The surgical retractor according to claim 12 wherein the distal end portion of the elongated sleeve member is configured for insertion at least partially into an intervertebral space between adjacent opposed vertebrae, and wherein the first and second supporting surfaces of each retractor arm are laterally spaced with respect to the longitudinal axis sufficient to contact the adjacent vertebrae during insertion thereof within the intervertebral space to at least maintain a desired predetermined distance therebetween.

16. A method for performing a surgical spinal procedure, comprising the steps of:

providing a laparoscopic surgical retractor including an elongated member having proximal and distal end portions and defining a longitudinal opening, the distal end portion including two spaced apart retractor arms having first and second supporting surfaces, the surgical retractor further including a valve assembly mounted to the proximal end portion of the elongated member and having, a valve member associated therewith;

introducing a surgical instrument within the opening of the surgical retractor whereby the valve member of the value assembly forms a substantially fluid tight seal about an outer surface thereof; and performing the surgical procedure adjacent the distracted vertebrae with the surgical instrument.

17. The method according to claim 16 wherein the valve assembly includes a converter having a seal member associated therewith and wherein the step of introducing includes inserting the surgical instrument within the converter such that the seal member forms a substantially fluid-tight seal about the surgical instrument.

18. The method according to claim 16 further including the steps of:

inserting an impactor instrument within the surgical retractor whereby upon insertion therein the valve assembly sealingly engages the impactor instrument;

impacting the proximal end portion of the impactor instrument such that corresponding engaging structure of the surgical retractor and the impactor instrument drives the surgical retractor within the adjacent vertebrae; and removing the impactor instrument from the surgical retractor.

19. The method according to claim 16 wherein the step of performing includes inserting an insertion instrument having a fusion implant mounted to a distal end portion thereof within the opening of the surgical retractor and mounting the implant with the insertion instrument within the adjacent vertebrae.

20. The method according to claim 19 further including the steps of:

introducing a drill instrument into the surgical retractor and advancing the drill instrument within the retractor to the disc space;

actuating the drill instrument such that the distal drill head cuts a bore in the vertebral bodies;

removing the drill instrument from the surgical retractor.

21. The method according to claim 20 further including a step of introducing a surgical tapping instrument into the surgical retractor to tap an internal thread within the bore defined between the adjacent vertebrae.

22. The surgical retractor according to claim 15 wherein the first and second support surfaces of each retractor arm define spacing distance therebetween at least equal to the height of the intervertebral space.

* * * * *